(12) United States Patent
Aicher et al.

(10) Patent No.: US 8,431,713 B2
(45) Date of Patent: *Apr. 30, 2013

(54) 2-AMINOPYRIDINE DERIVATIVES AS GLUCOKINASE ACTIVATORS

(75) Inventors: Thomas Daniel Aicher, Superior, CO (US); Steven Armen Boyd, Longmont, CO (US); Mark Joseph Chicarelli, Westminster, CO (US); Kevin Ronald Condroski, Lafayette, CO (US); Rustam Ferdinand Garrey, Loveland, CO (US); Ronald Jay Hinklin, Longmont, CO (US); Ajay Singh, Longmont, CO (US); Timothy M. Turner, Longmont, CO (US)

(73) Assignee: Array BioPharma, Inc., Boulder, CO (US)

( * ) Notice: Subject to any disclaimer, the term of this patent is extended or adjusted under 35 U.S.C. 154(b) by 873 days.

This patent is subject to a terminal disclaimer.

(21) Appl. No.: 12/524,327

(22) PCT Filed: Jan. 16, 2008

(86) PCT No.: PCT/US2008/051194
§ 371 (c)(1),
(2), (4) Date: Jul. 23, 2009

(87) PCT Pub. No.: WO2008/091770
PCT Pub. Date: Jul. 31, 2008

(65) Prior Publication Data
US 2010/0099713 A1   Apr. 22, 2010

Related U.S. Application Data

(60) Provisional application No. 60/897,385, filed on Jan. 24, 2007, provisional application No. 60/914,236, filed on Apr. 26, 2007.

(51) Int. Cl.
*A61K 31/44* (2006.01)
*C07D 213/55* (2006.01)

(52) U.S. Cl.
USPC .......................... 546/342; 514/270.7

(58) Field of Classification Search ............... 546/270.7; 514/342
See application file for complete search history.

(56) References Cited

U.S. PATENT DOCUMENTS

| 8,022,222 B2 * | 9/2011 | Aicher et al. | 546/270.7 |
| 8,022,223 B2 * | 9/2011 | Aicher et al. | 546/270.7 |
| 2010/0105659 A1 * | 4/2010 | Aicher et al. | 514/217.04 |

FOREIGN PATENT DOCUMENTS

| EP | 1598349 | 11/2005 |
| WO | 2007/089512 | 8/2007 |

* cited by examiner

*Primary Examiner* — John Mabry
(74) *Attorney, Agent, or Firm* — Banner & Witcoff, Ltd.

(57) ABSTRACT

Provided are compounds having the Formula I

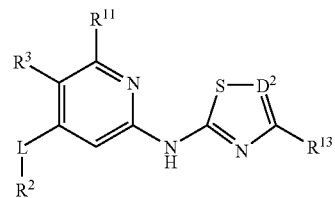

or salts thereof, wherein $R^2$, L, $R^3$, $R^{11}$, $D^2$ and $R^{13}$ are as defined herein, that are useful in the treatment and/or prevention of diseases mediated by deficient levels of glucokinase activity, such as diabetes mellitus. Also provided are methods of treating or preventing diseases and disorders characterized by underactivity of glucokinase or which can be treated by activating glucokinase.

2 Claims, No Drawings

2-AMINOPYRIDINE DERIVATIVES AS GLUCOKINASE ACTIVATORS

The present invention relates to novel compounds, to pharmaceutical compositions comprising the compounds, to a process for making the compounds and to the use of the compounds in therapy. More particularly, it relates to certain glucokinase activators useful in the treatment of diseases and disorders that would benefit from activation of glucokinase. This invention further relates to intermediates suitable for preparing compounds of this invention.

Glucokinase (hexokinase IV or D) is a glycolytic enzyme that plays an important role in blood sugar regulation related to the glucose utilization and metabolism in the liver and pancreatic beta cells. Serving as a glucose sensor, glucokinase controls plasma glucose levels. Glucokinase plays a dual role in reducing plasma glucose levels: glucose-mediated activation of the enzyme in hepatocytes facilitates hepatic glucose uptake and glycogen synthesis, while that in pancreatic beta cells ultimately induces insulin secretion. Both of these effects in turn reduce plasma glucose levels.

Clinical evidence has shown that glucokinase variants with decreased and increased activities are associated with diabetes of the young type (MODY2) and persistent hyperinsulinemic hypoglycemia of infancy (PHHI), respectively. Also, non-insulin dependent diabetes mellitus (NIDDM) patients have been reported to have inappropriately low glucokinase activity. Furthermore, overexpression of glucokinase in dietary or genetic animal models of diabetes either prevents, ameliorates, or reverses the progress of pathological symptoms in the disease. For these reasons, compounds that activate glucokinase have been sought by the pharmaceutical industry. A class of glucokinase activators that can lower the $K_m$ of glucose moderately to 2-5 mM at low activator concentrations is desirable.

It has now been found that aminothiazolyl- and amino-1,2,4-thiadiazolyl-substituted pyridine compounds having particularly desirable properties may be obtained by selecting particular N-(1-6C alkanoyl)-piperidin-4-yl groups as the substituent at the 4 or 3 position of the thiazole or thiadiazole ring, respectively.

Accordingly, one aspect of the present invention provides a compound of general Formula I

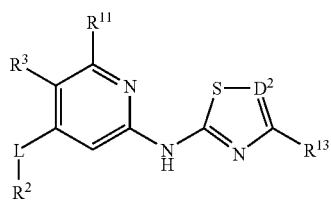

I or salts thereof, wherein:

L is O, S, SO, $SO_2$, CHOH, C(O), or $CH_2$;

$D^2$ is $CR^{12}$ or N;

$R^2$ is aryl, heteroaryl, saturated or partially unsaturated cycloalkyl, or saturated or partially unsaturated heterocyclyl (optionally substituted with oxo), wherein said aryl, heteroaryl, cycloalkyl and heterocyclyl are monocyclic or bicyclic and are further optionally substituted with one or more groups independently selected from $C_1$-$C_6$ alkyl, F, Cl, Br, I, $CF_3$, CN, $OR^6$, $C(=O)R^6$, $C(=O)OR^6$, $O(CH_2)_nC(=O)OR^6$, $C(=O)NR^6R^7$, $NO_2$ and (1-6C alkyl)$OR^6$;

$R^3$ is H, Br, $OR^6$, $SR^6$, $C(O)OR^6$, $C(O)NR^6R^7$, $C(O)R^6$, heteroaryl, or $C_1$-$C_6$ alkyl substituted with one or more groups independently selected from $V_n$-aryl, $V_n$—$OR^6$, $V_n$—$C(=O)OR^6$ and $V_n$—$NR^6R^7$;

each $R^6$ and $R^7$ is independently H, $C_1$-$C_6$ alkyl, saturated or partially unsaturated cycloalkyl, aryl, or heteroaryl, wherein said alkyl is optionally substituted with one or more groups independently selected from aryl, $V_n$-heterocyclyl [optionally substituted with $C(O)O(C_1$-$C_6$ alkyl)], $V_n$-heteroaryl, $V_n$—$C(=O)OR^8$, and $NR^8R^9$;

or $R^6$ and $R^7$ together with the atom to which they are attached form a saturated or partially unsaturated heterocyclic ring, wherein said heterocyclic ring optionally comprises one or more additional ring nitrogen heteroatoms, wherein said heterocyclic ring is optionally substituted with one or more groups independently selected from $C_1$-$C_6$ alkyl;

each $R^8$, $R^9$ and $R^{10}$ is independently H or $C_1$-$C_6$ alkyl;

$R^{11}$ is H or Cl;

$R^{12}$ is H, $C_1$-$C_6$ alkyl (optionally substituted with one or more groups independently selected from $V_n$—$OR^8$ or $V_n$—$C(=O)OR^8$), saturated or partially unsaturated cycloalkyl, saturated or partially unsaturated heterocyclyl, aryl, or heteroaryl (optionally substituted with $C_1$-$C_6$ alkyl);

$R^{13}$ is N-(1-6C alkanoyl)piperidin-4-yl;

each V is independently alkylene having from 1 to 4 carbons or alkenylene having from 2 to 4 carbons; and each n is independently 0 or 1.

Certain compounds of Formula I, including certain compounds described in the Examples, are useful intermediates for preparing additional compound of Formula I.

In certain embodiments, $R^3$ is H, Br, $OR^6$, $SR^6$, $C(O)OR^6$, $C(O)NR^6R^7$, $C(O)R^6$, heteroaryl, or $C_1$-$C_6$ alkyl substituted with one or more groups independently selected from $V_n$-aryl, $V_n$—$OR^8$, $V_n$—$C(=O)OR^8$ and $V_n$—$NR^8R^9$.

In certain embodiments, each $R^6$ and $R^7$ is independently selected from the values above, other than an alkyl group substituted by one more groups selected from aryl and $NR^8R^9$, and $R^2$ is independently selected from the values above, other than a group substituted by (1-6 Calkyl)$OR^6$.

In certain embodiments, L is O.
In certain embodiments, L is S.
In certain embodiments, L is SO.
In certain embodiments, L is $SO_2$.
In certain embodiments, L is CHOH.
In certain embodiments, L is C(O).
In certain embodiments, L is $CH_2$.
In certain embodiments, $R^{11}$ is H.
In certain embodiments, $R^{11}$ is Cl.
In certain embodiments, D is N.
In certain embodiments, D is $CR^{12}$.
In certain embodiments of Formula I, $R^{12}$ is H, methyl, ethyl, propyl, isopropyl, butyl, isobutyl, or t-butyl.
In particular embodiments, $R^{12}$ is H.
In certain embodiments of Formula I, $R^2$ is aryl.
In certain embodiments, $R^2$ is phenyl optionally substituted with one or more groups independently selected from F, Cl, CN, $CF_3$, —$OR^6$, —$CO_2R^6$, —$O(CH_2)_nC(=O)OR^6$, —$C(=O)NR^6R^7$, (1-6C) alkyl and (1-6C alkyl)$OR^6$.

Particular examples of (1-6C) alkyl substituents include methyl, ethyl and isopropyl.

Examples of phenyl substituents having the formula —$OR^6$ include groups wherein $R^6$ is H or a (1-6C) alkyl group. In other embodiments, $R^6$ is a phenyl group. Examples of —$OR^6$ groups include OH, OMe, and OPh. In other embodiments, $R^6$ is an alkyl group substituted with an aryl group, for example a phenyl group. A particular example of —$OR^6$ is $OCH_2Ph$.

Examples of phenyl substituents having the formula —$C(=O)OR^6$ include groups wherein $R^6$ is H or a 1-6C alkyl group optionally substituted with OH. Particular examples of —C(=O)OR$^6$ groups include $CO_2H$, $CO_2Me$, $CO_2Et$, Examples of phenyl substituents having the formula —O(CH$_2$)C(O)OR$^6$ include groups wherein R$^6$ is H or a 1-6C alkyl group. Particular examples include —O(CH$_2$)C(O)OC (CH$_3$)$_3$ and —O(CH$_2$)C(O)OH.

Examples of phenyl substituents having the formula —C(=O)NR$^6$R$^7$ include groups wherein R$^6$ and R$^7$ are independently H or a 1-6C alkyl group. In certain embodiments, R$^6$ is H or Me. In certain embodiments, R$^7$ is an alkyl group is substituted with —NR$^8$R$^9$ (wherein R$^8$ and R$^9$ are independently H or 1-6C alkyl), a 5-membered heteroaryl having 1-2 nitrogen atoms, or a 5-6 membered heterocycle having 1-2 ring heteroatoms independently selected from N and O. Particular examples of —C(=O)NR$^6$R$^7$ groups include C(O)NHCH$_2$CH$_2$NMe$_2$, C(O)NMeCH$_2$CH$_2$NMe$_2$, C(O)NMeCH$_2$CH$_2$CH$_2$NMe$_2$, C(O)NHCH$_2$CH$_2$NHCH(CH$_3$)$_2$, C(O)CH$_2$CH$_2$CH$_2$(4-morpholinyl), C(O)NHCH$_2$CH$_2$(1-pyrrolidinyl), C(O)NHCH$_2$CH$_2$(imidazole-4-yl), and C(O)NHCH$_2$CH$_2$NHMe.

Further examples of phenyl substituents having the formula —C(=O)NR$^6$R$^7$ include groups wherein —NR$^6$R$^7$ forms a 5-6 membered heterocyclic ring optionally having a nitrogen atom and optionally having a second heteroatom selected from N and O. Particular values include pyrrolidinyl, piperidinyl, piperazinyl and morpholinyl rings. In certain embodiments the heterocyclic ring is substituted with a 1-6C alkyl group. Particular examples include C(O)-(pyrrolidinyl), C(O)-(4-methylpiperazin-1-yl) and C(O)-(4-ethylpiperazin-1-yl).

Examples of phenyl substituents represented by (1-6C alkyl)OR$^6$ include groups wherein R$^6$ is H or 1-6C alkyl. Particular values include CH$_2$OH and CH$_2$CH$_2$OH.

In particular embodiments of Formula I, R$^2$ is phenyl optionally substituted with one or more groups independently selected from Cl, F, CN, Me, iPr, CF$_3$, —OCH$_3$, —OH,0 —OCH$_2$CH$_2$OH, —CH$_2$OH, —OCH$_2$CO$_2$H, —OCH$_2$CO$_2$(t-Bu), —CO$_2$Me, —CO$_2$Et, —CO$_2$H, —C(O)NHCH$_2$CH$_2$NMe$_2$, —C(O)NHCH$_2$CH$_2$CH$_2$N(CH$_3$)$_2$, —C(O)N(Me)CH$_2$CH$_2$N(CH$_3$)$_2$, —C(O)NHCH$_2$CH$_2$NHCH(CH$_3$)$_2$, —C(O)NH(CH$_2$)$_3$(N-morpholinyl), —C(O)(N-pyrrolidinyl), —C(O)NHCH$_2$CH$_2$(imidazolyl), —OCH$_2$C(O)OH,

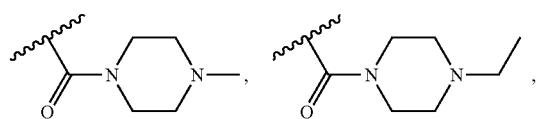

C(O)NHCH$_2$CH$_2$-pyrrolidinyl, C(O)NHCH$_2$CH$_2$NHMe, OCH$_2$Ph, and CH$_2$CH$_2$OH.

Further exemplary embodiments of R$^2$ include, but are not limited to, the structures:

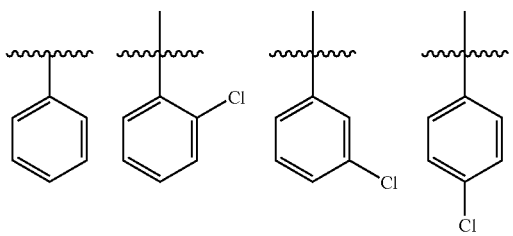

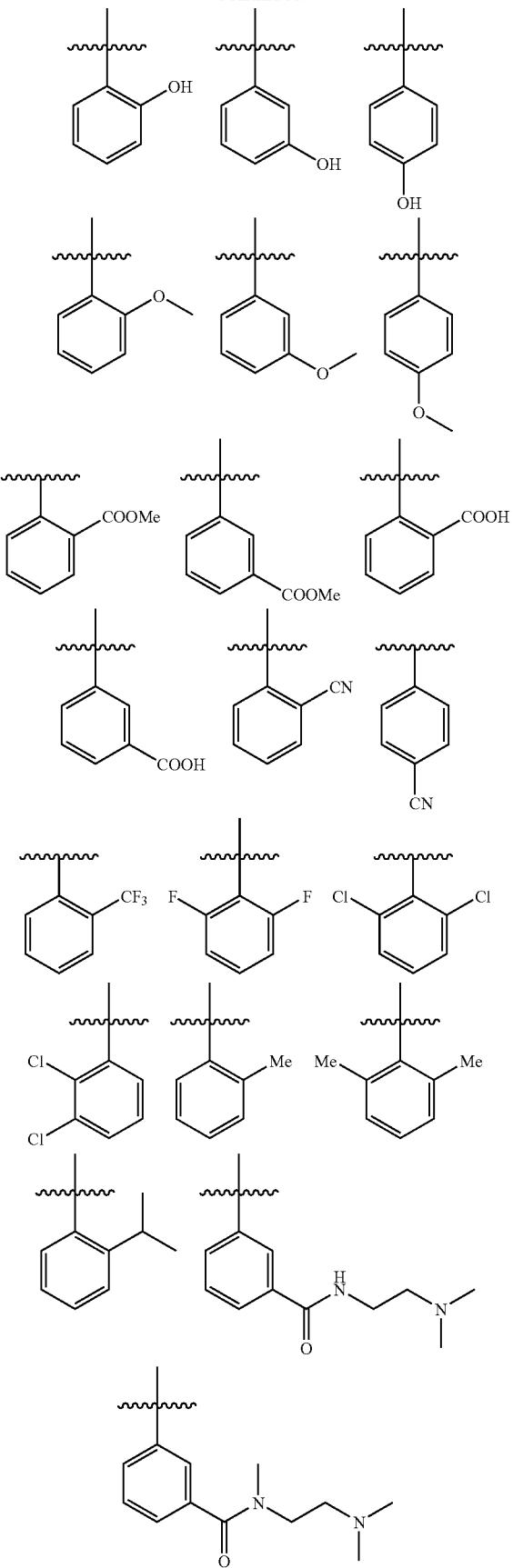

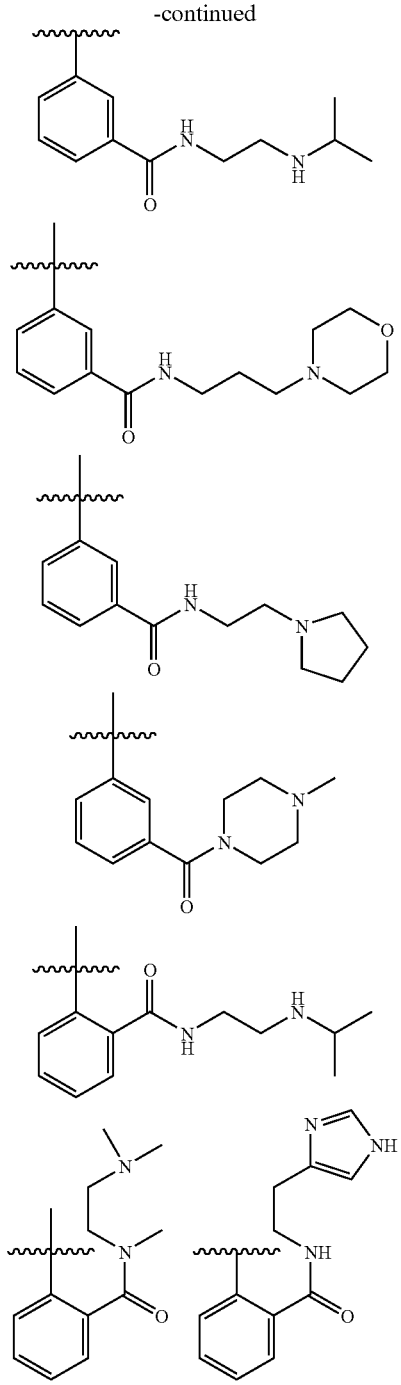
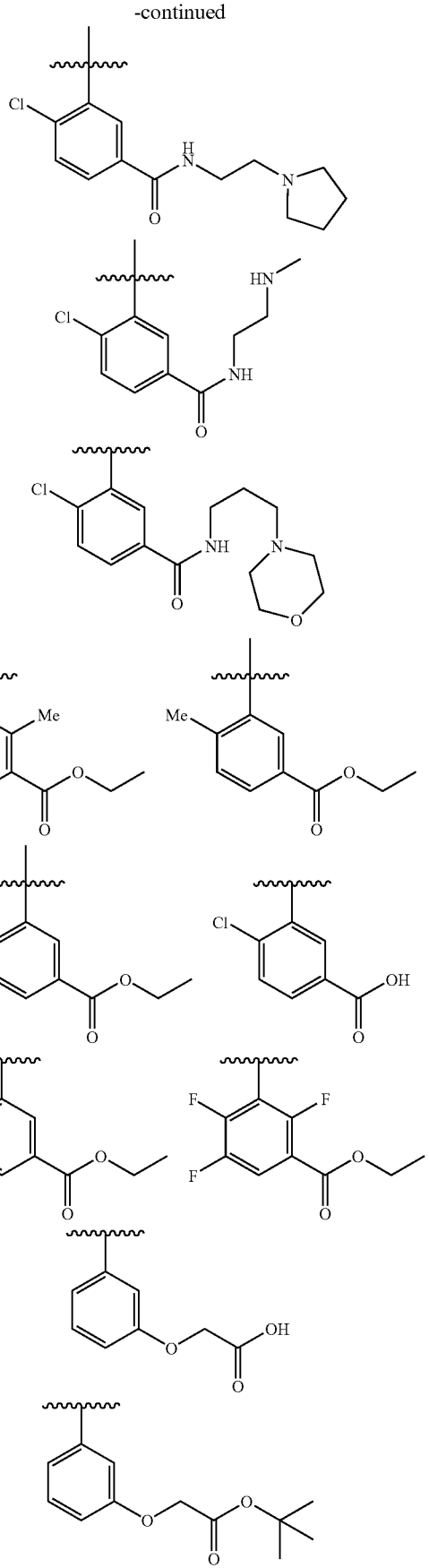

-continued

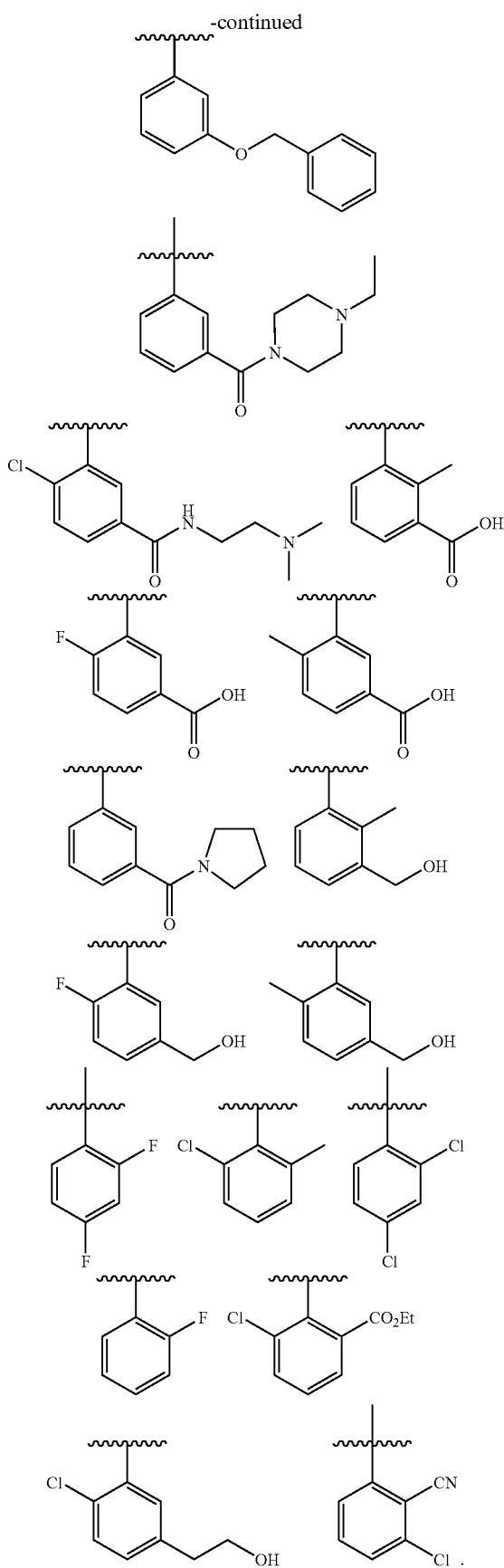

In other embodiments, R² is a 5-6 membered heteroaryl ring having 1-3 heteroatoms independently selected from N and O (with the proviso that the ring does not contain two O atoms attached directly to each other). Examples of heteroaryl rings include 2-pyridyl, 3-pyridyl, 4-pyridyl, 2-imidazolyl, 3-furyl, 1,2,4-oxadiazol-5-yl, 1,3,4-oxadiazol-2-yl, and 2-oxazolyl.

In particular embodiments, the heteroaryl group is substituted with one or two groups independently selected from NO₂, Cl, Br, CN, CF₃, and 1-6C alkyl.

In particular embodiments, R² is selected from the structures:

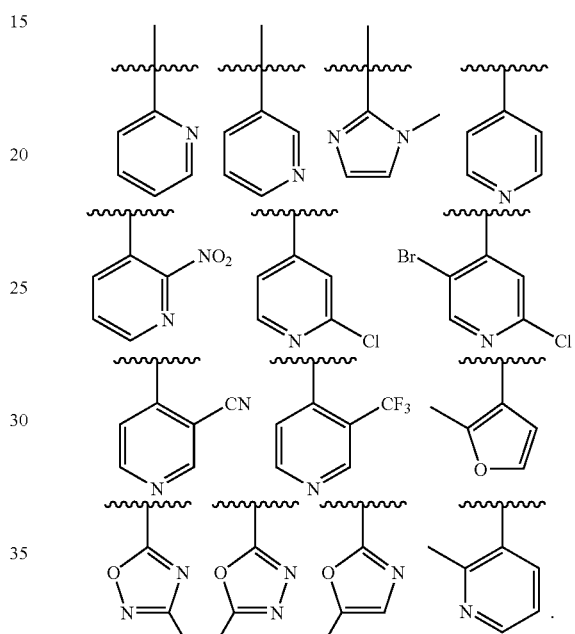

In another embodiment, R² is a partially unsaturated 5 membered heterocyclic ring. In certain embodiments, there heterocyclic ring has one or two ring heteroatoms, for example, 1-2 nitrogen atoms, such as a 4,5-dihydro-1H-pyrazolyl ring. In certain embodiments, the heterocyclic ring is substituted with oxo. A particular example of R² is the structure:

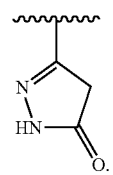

In other embodiments, R² is a 9-10 membered heteroaryl ring having a nitrogen atom and optionally having 1 to 2 additional ring heteroatoms independently selected from N, O and S (with the proviso that the ring does not contain a O—O or S—S bond). In certain embodiments, the heteroaryl ring is a bicyclic ring. In certain embodiments, the bicyclic ring is quinolyl, isoxazolo[5,4-b]pyridyl, thienopyridyl, or pyrazolopyrimidyl.

In certain embodiments, the bicyclic heteroaryl ring is substituted with C₁-C₆ alkyl (for example, methyl).

Further exemplary embodiments when $R^2$ is represented by a 9-10 membered heteroaryl ring include the structures:

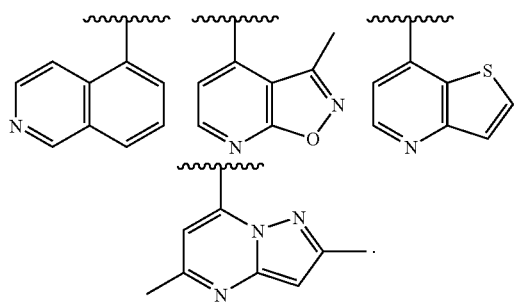

In certain embodiments, $R^2$ is a partially unsaturated 9-10 membered bicyclic heterocyclic ring having 1-3 nitrogen atoms, such as a 5,6,7,8-tetrahydropyrido[4,3-d]pyrimidyl ring. In certain embodiments, the bicyclic heterocyclic ring is substituted with C(O)O-tBu. Exemplary embodiments include the structures:

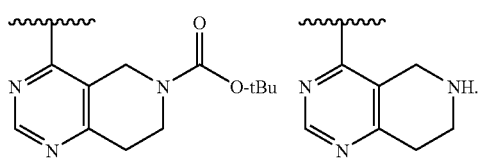

In certain embodiments, $R^2$ is a 5-6 membered cycloalkyl ring optionally substituted with 1-6C alkyl. In certain embodiments, $R^2$ is cyclopentyl or cyclohexyl optionally substituted with methyl. In particular embodiments, $R^2$ is cyclopentyl, cyclohexyl or 2-methylcyclohexyl.

In certain embodiments of Formula I, $R^3$ is H, Br, $OR^6$, $SR^6$, $C(O)OR^6$, $C(O)NR^6R^7$, $C(O)R^6$, a 5-6 membered heteroaryl group having at least one ring nitrogen atom, (1-6C alkyl)$CO_2R^6$, (1-6C alkyl)$OR^6$, (1-6C alkyl)$NR^6R^7$, (2-6C alkenyl)$NR^6R^7$ or (1-6C alkyl)Ar.

In certain embodiments of Formula I, $R^3$ is a group having the formula $SR^6$ wherein $R^6$ is cycloalkyl, aryl, heteroaryl, (1-6C alkyl)$C(O)OR^8$, (1-6C alkyl)heteroaryl, or (1-6C alkyl)heterocyclyl [wherein the heterocyclyl group is optionally substituted with $CO_2$-tBu].

A particular example of $SR^6$ when represented by S-cycloalkyl includes S—($C_3$-$C_6$ cycloalkyl). A particular value includes S-cyclohexyl.

A particular example of $SR^6$ when represented by S-aryl includes S-phenyl. In certain embodiments, the aryl group is substituted by O-(1-6 alkyl), for example methoxy. A particular example includes S-(3-methoxyphenyl).

Particular examples of $SR^6$ when represented by S-heteroaryl include groups wherein the heteroaryl moiety is a 5-6 membered ring having a nitrogen atom and optionally having an additional atom selected from N and S, for example, pyridyl, pyrazinyl and thienyl rings. Particular examples include the structures:

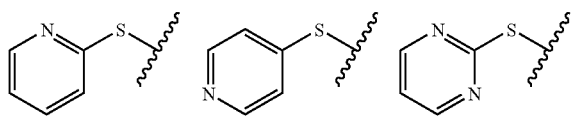

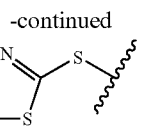

Further examples of $SR^6$ when represented by S-heteroaryl include groups wherein the heteroaryl moiety is a thienopyridyl ring. A particular value is the structure:

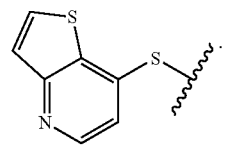 [SMILES: *Sc1ccnc2ccsc12]

Examples of $SR^6$ when represented by —S-(1-6C alkyl)C(O)$OR^8$ include groups wherein $R^8$ is 1-6C alkyl. A particular value is S—$CH_2CH_2C(O)OCH_3$.

Examples of $SR^6$ when represented by —S-(1-6C alkyl)-heteroaryl include groups wherein the heteroaryl moiety is a 6 membered heteroaryl, such as a pyridyl or pyrimidyl group. A particular value includes S—$CH_2$-(2-pyridyl).

Examples of $SR^6$ when represented by —S-(1-6C alkyl)-heterocyclyl include groups wherein the heterocycle is a 5-6 membered azacycle, such as a piperidyl ring. In other embodiments, the heterocycle is a 5-6 membered heterocycle having 2 ring nitrogen atoms. In certain embodiments the azacycle is substituted with a $CO_2$-tBu group. Particular values include:

In certain embodiments, $R^3$ is (1-6C) alkyl substituted with one or more groups independently selected from $V_n$aryl, $V_n$—$OR^6$, $V_n$—C(=O)$OR^6$ and $V_n$—$NR^6R^7$. In certain embodiments, V is alkylene having from 1-4 carbons. In certain embodiments, n is 1. In other embodiments, n is 0.

In other embodiments, $R^3$ is (1-6C alkyl)$OR^6$ wherein $R^6$ is H or alkyl. In a particular embodiment, $R^3$ is $CH_2OH$.

In other embodiments of Formula I, $R^3$ is a group having the formula $OR^6$. In certain embodiments, $R^6$ is H or 1-6C alkyl. In particular embodiments, $R^3$ is OH or $OCH_3$.

In certain embodiments of Formula I, $R^3$ is (1-6C alkyl)-Aryl. In certain embodiments, Aryl is phenyl. A particular value of $R^3$ includes a benzyl group.

In other embodiments of Formula I, $R^3$ is (1-6C alkyl)-$NR^6R^7$. In certain embodiments, $R^6$ and $R^7$ are independently H, 1-6C alkyl, (1-6C alkyl)N(1-6C alkyl)$_2$ or (3-6C)cycloalkyl. Particular values of $R^3$ include CH=CHCH$_2$CH$_2$N(CH)$_3$, $CH_2NMe_2$, $CH_2NH$—cyclohexyl, and $CH_2NHCH_2CH_2NMe_2$.

In other embodiments, $R^3$ is (1-6C alkyl)-$NR^6R^7$ wherein $NR^6R^7$ forms a 5-6 membered azacyclic ring, for example a piperidyl ring. In other embodiments, $NR^6R^7$ forms a 5-6 membered heterocyclic ring having 2 ring nitrogen atoms. A particular value for $R^3$ includes $CH_2$-(1-piperidyl).

In other embodiments, $R^3$ is a 5-6 membered heteroaryl group having at least one ring nitrogen atom.

In other embodiments, $R^3$ is a 6 membered heteroaryl group, such as a pyridyl group. Particular values for $R^3$ include 2-pyridyl, 3-pyridyl, and 4-pyridyl.

In other embodiments, $R^3$ is (1-6C alkyl)C(=O)OR$^6$. In certain embodiments, $R^6$ is H or (1-6C)alkyl. For example, in certain embodiments $R^3$ is CH$_2$CH$_2$CO$_2$Me.

In certain embodiments of Formula I, $R^3$ is a group having the formula CO$_2$R$^6$. In certain embodiments, $R^6$ is H or 1-6C alkyl. Particular values of $R^3$ include CO$_2$H and CO$_2$Et.

In certain embodiments of Formula I, $R^3$ is a group having the formula COR$^6$. In certain embodiments, $R^6$ is H or (1-6C) alkyl. A particular value of $R^3$ is C(O)H.

In certain embodiments of Formula I, $R^3$ is a group having the formula C(O)NR$^6$R$^7$. In certain embodiments, $R^6$ and $R^7$ are independently H or 1-6C alkyl optionally substituted with —N(1-6C alkyl)$_2$. In other embodiments, NR$^6$R$^7$ forms a 5-6 membered azacyclic or diazacyclic ring optionally substituted with 1-6C alkyl, for example an optionally substituted piperidyl ring. Particular values of $R^3$ include C(O)NHCH$_2$CH$_2$N(CH$_3$)$_2$ and C(O)(N-ethylpiperazin-4-yl).

In certain embodiments of Formula I, $R^3$ is Br.

In certain embodiments of Formula I, $R^3$ is H.

The compound of Formula I includes compounds of formula Ia

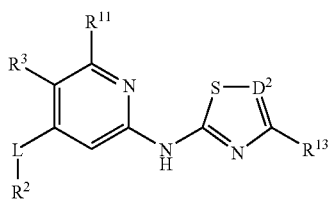

Ia wherein

L is O, S, SO, SO$_2$, CHOH, C(O), or CH$_2$;

D$^2$ is CR$^{12}$ or N;

$R^2$ is aryl, 3-pyridyl or 8-quinolinyl, wherein said aryl, pyridyl and quinolinyl are optionally substituted with one or more groups independently selected from 1-6C alkyl, Cl, CN, and C(=O)NR$^6$R$^7$;

$R^3$ is H, Br, S-aryl, O-aryl, CH$_2$-aryl, S-heteroaryl, O-heteroaryl or CH$_2$-heteroaryl, wherein said aryl and heteroaryl portions are optionally substituted with one or more groups independently selected from (1-3C) alkyl, F, Cl, Br, CN, CF$_3$, and O-(1-3C alkyl);

$R^6$ and $R^7$ are independently H, 1-6C alkyl, -(1-6C alkyl)NH$_2$, -(1-6C alkyl)NH(1-6C alkyl), -(1-6C alkyl)N(1-6C alkyl)$_2$, -(1-6C alkyl)-heteroaryl and -(1-6C alkyl)-heterocycle;

$R^{11}$ is H or Cl;

$R^{12}$ is H or 1-6C alkyl; and $R^{13}$ is N-(1-6C alkanoyl)-piperidin-4-yl.

In certain embodiments of formula Ia, D$^2$ is CR$^{12}$. In certain embodiments, D$^2$ is CH.

In certain embodiments of formula Ia, D$^2$ is CR$^{12}$ and R$^{12}$ is 1-6C alkyl. Examples of alkyl groups include methyl, ethyl, propyl, isopropyl, butyl, isobutyl, and t-butyl.

In certain embodiments of formula Ia, D$^2$ is N.

In certain embodiments of formula Ia, L is O.

In certain embodiments of formula Ia, L is S.

In certain embodiments of formula Ia, L is SO.

In certain embodiments of formula Ia, L is SO$_2$.

In certain embodiments of formula Ia, L is CHOH.

In certain embodiments of formula Ia, L is C(O).

In certain embodiments of formula Ia, L is CH$_2$.

In certain embodiments of formula Ia, R$^{11}$ is H.

In certain embodiments, R$^{11}$ is Cl.

In certain embodiments of formula Ia, $R^2$ is aryl optionally substituted with one or more groups independently selected from Cl, 1-6C alkyl, and C(=O)NR$^6$R$^7$. In certain embodiments, the aryl group is a phenyl group optionally substituted with one or more groups independently selected from Cl, 1-6C alkyl, and C(=O)NR$^6$R$^7$.

Examples of aryl substituents of formula Ia having the formula —C(=O)NR$^6$R$^7$ include groups wherein R$^6$ is H, and R$^7$ is H, 1-6C alkyl, -(1-6C alkyl)NH$_2$, -(1-6C alkyl)NH (1-6C alkyl), -(1-6C alkyl)N(1-6C alkyl)$_2$, -(1-6C alkyl)-heteroaryl or -(1-6C alkyl)-heterocycle.

Examples of R$^7$ of formula Ia when represented by -(1-6C alkyl)-heterocycle include groups wherein the heterocycle is a 5-6 membered ring having 1-2 atoms independently selected from N and O. A particular example of the heterocyclic ring is a morpholinyl group.

Examples of R$^7$ of formula Ia when represented by -(1-6C alkyl)-heteroaryl include groups wherein the heteroaryl is a 5-membered ring having 1-2 nitrogen atoms. A particular value for the heteroaryl is an imidazolyl group.

In certain embodiments of formula Ia, $R^2$ is a phenyl group optionally substituted with one or more groups independently selected from Cl, Me, —C(O)NHCH$_2$CH$_2$NMe$_2$, —C(O)NHCH$_2$CH$_2$CH$_2$N(CH$_3$)$_2$, —C(O)N(Me)CH$_2$CH$_2$N(CH$_3$)$_2$, —C(O)NHCH$_2$CH$_2$NHCH(CH$_3$)$_2$, —C(O)NH(CH$_2$)$_3$(N-morpholinyl), and —C(O)NHCH$_2$CH$_2$ (imidazolyl).

In particular embodiments of formula Ia, $R^2$ is phenyl optionally substituted with one or two groups independently selected from Cl, Me and —C(O)NHCH$_2$CH$_2$NMe$_2$.

In a particular embodiment, $R^2$ is phenyl optionally substituted with one or two groups selected from Cl and Me.

Particular values of $R^2$ of formula Ia include the structures:

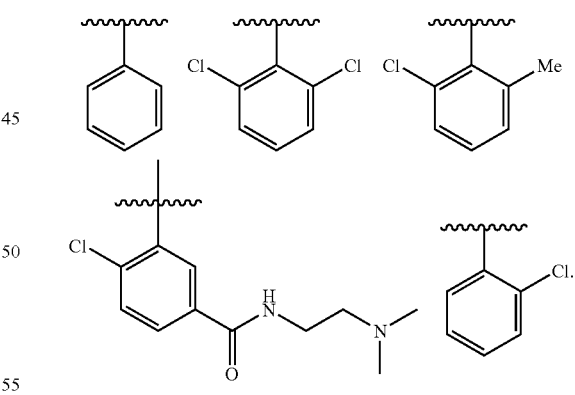

In other embodiments of formula Ia, $R^2$ is 3-pyridyl optionally substituted with one or more groups independently selected from (1-6C alkyl), CN, and C(=O)NR$^6$R$^7$, wherein the C(=O)NR$^6$R$^7$ group is as defined above.

Exemplary embodiments of formula Ia of $R^2$ include 3-pyridyl optionally substituted with one or more groups independently selected from methyl, CN, —C(O)NHCH$_2$CH$_2$NMe$_2$, —C(O)NHCH$_2$CH$_2$CH$_2$N(CH$_3$)$_2$, —C(O)N(Me)CH$_2$CH$_2$N (CH$_3$)$_2$, —C(O)NHCH$_2$CH$_2$NHCH(CH$_3$)$_2$, —C(O)NH (CH$_2$)$_3$(N-morpholinyl), and —C(O)NHCH$_2$CH$_2$ (imidazolyl).

In particular embodiments of formula Ia, R² is 3-pyridyl optionally substituted with one or two groups independently selected from methyl, CN and —C(O)NHCH₂CH₂NMe₂.

Particular values for R² of formula Ia include the structures:

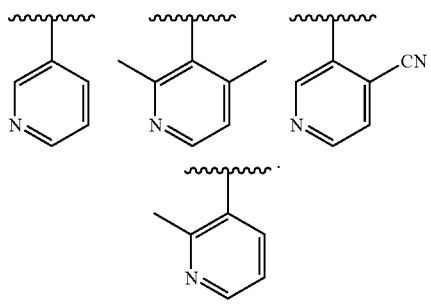

Particular mention is made of 2-methylpyrid-1-yl.

In certain embodiments of formula Ia, R² is 8-quinolinyl.

In certain embodiments of formula Ia, R³ is H.

In certain embodiments of formula Ia, R³ is Br.

In certain embodiments of formula Ia, R³ is S-aryl optionally substituted with one or more groups independently selected from (1-3C) alkyl, F, Cl, Br, CN, CF₃, and O-(1-3C alkyl). In certain embodiment, the aryl group is phenyl. In certain embodiments, the phenyl group is substituted with an O-(1-3C alkyl) group, for example a methoxy group.

Particular values for R³ of formula Ia include S-phenyl and S-(3-methoxyphenyl).

In certain embodiments of formula Ia, R³ is S-heteroaryl optionally substituted with one or more groups independently selected from (1-3C) alkyl, F, Cl, Br, CN, CF₃, and O-(1-3C alkyl). Exemplary embodiments of R³ when represented by S-heteroaryl include groups wherein the heteroaryl moiety is a 5-6 membered ring having a nitrogen atom and optionally having an additional atom selected from N and S, for example, pyridyl, pyrimidyl and thiazolyl rings.

Particular values for R³ of formula Ia include the structures:

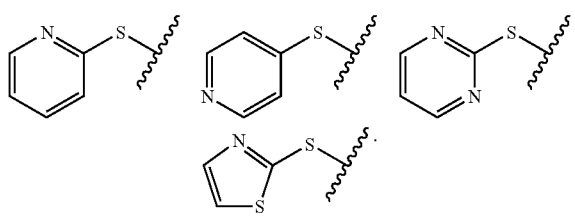

Particular mention is made of S-pyrid-2-yl.

In certain embodiments of formula Ia, R³ is S-heteroaryl wherein the heteroaryl portion is a thienopyridyl ring. A particular example of R³ includes the structure:

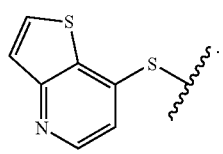 [SMILES: *Sc1ccnc2ccsc12]

In other embodiments of formula Ia, R³ is O-aryl optionally substituted with one or more groups independently selected from (1-3C)alkyl, F, Cl, Br, CN, CF₃, and O-(1-3C alkyl). In certain embodiments, the aryl moiety is a phenyl group. A particular value for R³ is O-phenyl.

In certain embodiments of formula Ia, R³ is O-heteroaryl optionally substituted with one or more groups independently selected from (1-3C)alkyl, F, Cl, Br, CN, CF₃, and O-(1-3C alkyl) A particular value of the heteroaryl is a 2-pyridyl, 3-pyridyl or 4-pyridyl group.

In certain embodiments of formula Ia, R³ is CH₂-aryl optionally substituted with one or more groups independently selected from (1-3C) alkyl, F, Cl, Br, CN, CF₃, and O-(1-3C alkyl).

A particular value for R³ of formula Ia is CH₂-phenyl.

In certain embodiments of formula Ia, R³ is CH₂-heteroaryl optionally substituted with one or more groups independently selected from (1-3C)alkyl, F, Cl, Br, CN, CF₃, and O-(1-3C alkyl). A particular value of the heteroaryl is a 2-pyridyl, 3-pyridyl or 4-pyridyl group.

A particular subset of compounds of Formula Ia have the general structure of Formula Ib:

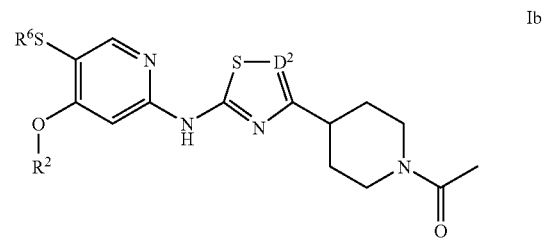

wherein R² and R⁶ are as defined for Formula Ia, and D² is N or CH.

It has been found that certain compounds of Formula I have increased cell permeability relative to corresponding compounds lacking the N-acyl moiety on the piperidinyl group. The cell permeability can be measured by methods well known to persons skilled in the art, for example, in a membrane-based drug assay such as a Caco-2 assay (see Brayden, D. J., Pharmaceutical News, 1997, 4, 11-15; Volpe, D. A., et al., Pharmacopeial Forum, 2001, 27, 2916-2922; Le Ferrec, E., et al., Altern. Lab. Anim. 2001, 29, 649-668). In particular, it was found that certain compounds of Formula Ia have increased cell permeability relative to corresponding compounds lacking the N-acyl moiety on the piperidinyl group.

It has also been found that certain compounds of Formula I have improved bioavailability, for example, increased exposure (i.e., increased levels of the parent drug in the plasma over time). In particular, it was found that certain compounds of Formula Ia have increased bioavailability relative to corresponding compounds lacking the N-acyl moiety on the piperidinyl group. A particular subset of such compound are certain compounds of Formula Ib.

The term "alkanoyl" as used herein, refers to the group —C(=O)-(1-6C alkyl), wherein the alkyl portion is of the straight or branched configuration. Exemplary alkanoyl groups include, but are not limited to, acetyl (ethanoyl), n-propanoyl, n-butanoyl, 2-methylpropanoyl and n-pentanoyl.

The term "alkyl" as used herein refers to a saturated linear or branched-chain monovalent hydrocarbon radical of one to six carbon atoms. Examples include, but are not limited to, methyl, ethyl, 1-propyl, 2-propyl, 1-butyl, 2-methyl-1-propyl, t-butyl, 1-pentyl, and the like.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Synthesis of Glucokinase Activators

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

For illustrative purposes, Schemes A-I show general methods for preparing the compounds of the present invention as well as key intermediates. For a more detailed description of the individual reaction steps, see the Examples section below.

Scheme A shows a method of preparing compound (3A) of Formula I having a thiazolyl group. To prepare compound (3A), a 2-aminoheterocycle (1) is reacted with benzoylisothiocyanate to afford a benzoylthiourea intermediate, which is hydrolyzed to the thiourea (2) with a base such as, but not limited to, potassium carbonate in a suitable solvent such as, but not limited to, ethanol. Alternatively, the aminoheterocycle (1) can be treated with an inorganic or ammonium isothiocyanate, e.g., Meckler's procedure, in the presence of an acid to afford the thiourea (2) in one step. Treatment of the thiourea (2) with an α-haloketone $R^{13}COCHR^{12}X$, wherein $X$=OTs, Cl, Br, I, or $NR_3$ (wherein R=1-6C alkyl), in a suitable base such as triethylamine, Hunig's base, DBU, alkali carbonate, sodium hydroxide, etc. and a suitable solvent such as ethanol affords the thiazole (3A). If the desired α-halo ketone $R^{13}COCHR^{12}X$ is not commercially available, it can be prepared by various methods known to those skilled in the art. Examples include, but are not limited to, bromination of commercially or readily synthesized methyl ketones (*Tetrahedron* (1970) 5611-5615; *Organic Synthesis* (1946) 13-15; *Tetrahedron* (1990) 2943-2964), diazomethane treatment of carbonyl chlorides, oxidation of 1-chloro-2-alkanols, bromination of silyl enol ethers, or halogenation of β-keto esters followed by decarboxylation.

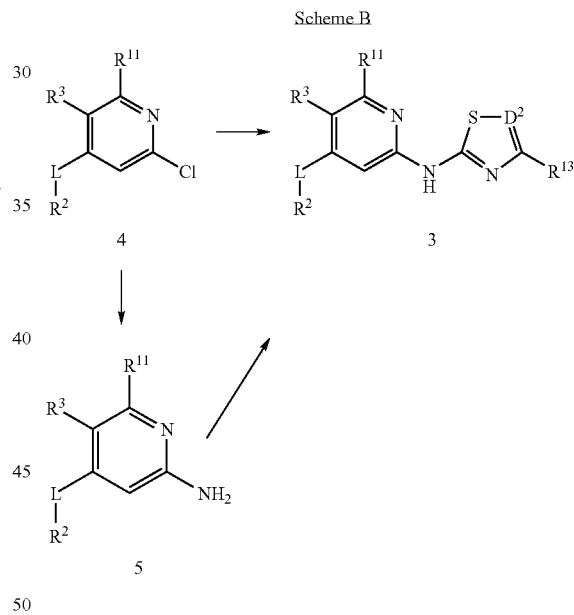

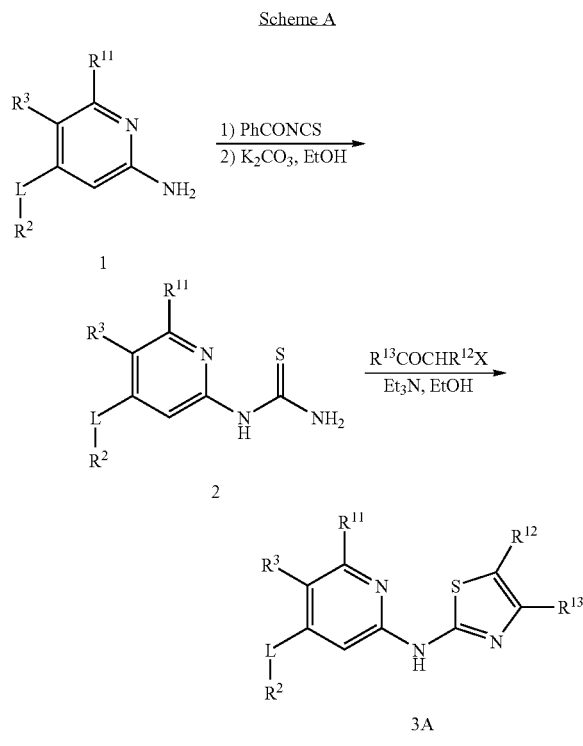

Scheme B shows a method of preparing a compound of Formula I having a thiazolyl or 1,2,4-thiadiazolyl group. According to Scheme B, compound (4) can be converted directly to a compound (3) of Formula I upon treatment with $R^1NH_2$ (wherein $R^1$ is thiazol-2-yl or 1,2,4-thiadiazol-5-yl) via base catalysis or via copper or palladium catalysis; i.e., the Buchwald reaction. Alternatively, 2-haloheterocycle (4) can be converted to compound (5) by the method of Hartwig et al. (for an example of this transformation via analogy see: *Organic Letters* (2001) 2729-2732), or by treatment with a Pd catalyst and benzophenone imine, or by heating in the presence of ammonia (or $NH_2PG$ where PG is a protecting group). Compound (5) can be converted to compound (3) of Formula I upon reaction with a thiazolyl halide or thiadiazolyl halide in the presence of a base catalyst or metal (e.g., copper or palladium) catalyst.

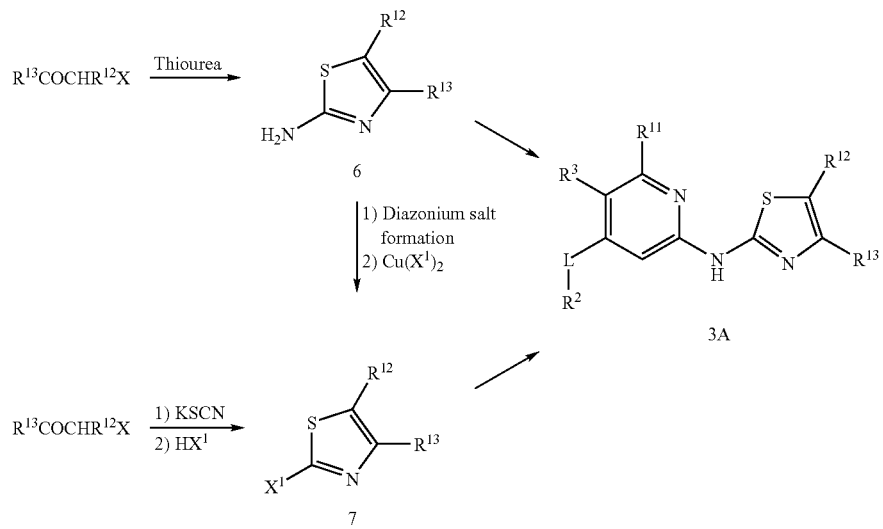

Scheme C shows a method of preparing 2-aminothiazole and 2-bromothiazole intermediates (6) and (7), respectively, which are suitable for use in preparing compounds of Formula I as shown in Scheme B. According to Scheme C, α-haloketone $R^{13}COCHR^{12}X$ can be treated with thiourea in the presence of a suitable base such as potassium carbonate or triethylamine in an appropriate solvent such as DMF or ethanol to afford aminothiazole (6). The aminothiazole (6) can be converted to a diazonium salt intermediate by numerous methods including, but not limited to, treatment with sodium nitrite in acid or isobutylnitrite. Treatment of the in situ diazonium salt with $Cu(X^1)_2$ ($X^1$=Cl or Br) or HBr affords the corresponding 2-halothiazole (7). Alternatively, using the Hantzsch synthetic method, the α-haloketone $R^{13}COCHR^{12}X$ can be treated first with KSCN, then with HX wherein X is Cl or Br, to provide the 2-halothiazole (7). The 2-halothiazole compounds (6) and (7) can be converted into compound (3A) by the methods shown in Scheme B.

Scheme D shows a method of preparing 5-amino-1,2,4-thiadiazole and 5-chloro-1,2,4-thiadiazole intermediates (13) and (14), respectively, which are suitable for use in preparing compounds of Formula I as shown in Scheme B. According to Scheme D, primary amide (12) can be converted into 5-amino-1,2,4 thiadiazole (13) by heating with KSCN in an appropriate solvent such as methanol or ethanol (*Adv. Heterocycl. Chem.*, (1982) 32, 285). Formation of the diazonium salt of compound (13), followed by treatment of the in situ diazonium salt with $CuCl_2$ affords the corresponding 5-chloro-1,2,4-thiadiazole (14). The corresponding bromo derivative can also be synthesized through the use of $CuBr_2$. Alternatively, reaction of amidine (15) with perchloromethyl mercaptan affords 5-chloro-1,2,4-thiadiazole (13) (*Bioorg. Med. Chem.*, (2003) 11, 5529-5537). Intermediates (13) and (14) can be converted into compound (3C) of Formula I by the method shown in Scheme B.

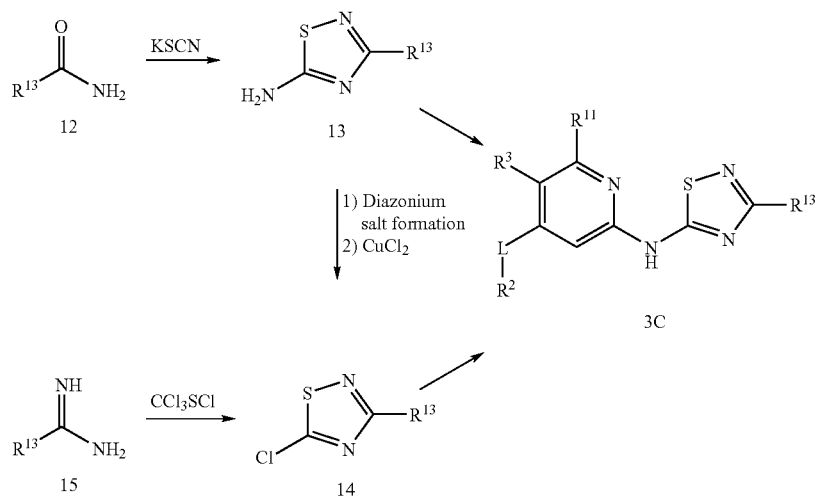

Scheme E

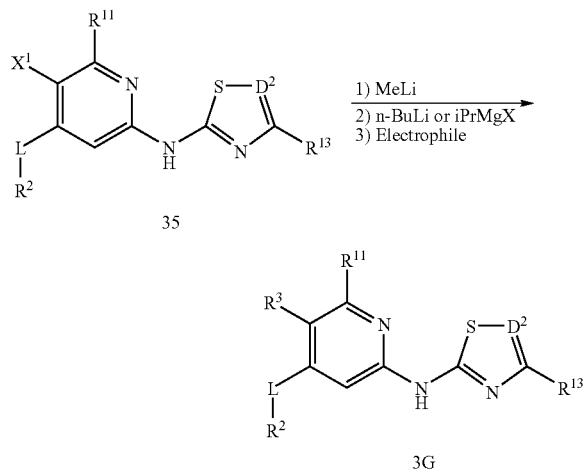

35

3G

Scheme E shows an alternative method of preparing compound (3G) of Formula I. According to Scheme E, the halo-substituted heterocycle (35) (prepared by the method of Scheme A or B) wherein $X^1$=Cl, Br or I, is first treated with an appropriate amount of methyl lithium solution to remove exchangeable proton(s), and then transmetalated with an alkyl lithium reagent such as n-BuLi, sec-butyl or tent-butyl lithium, or a Grignard reagent such as, i-PrMg-halide. The resulting anion is then quenched with an electrophile to provide compound (3G). Suitable electrophiles include, but are not limited to: 1) aldehydes, 2) nitriles, 3) N-methoxy-N-methylamides (Weinreb amides), 4) dialkyldisulphides, 5) hexachloroethane, 6) trialkyl boronates, 7) sulphonyl chlorides, 8) sulfamyl chlorides, 9) isocyanates, 10) carbon dioxide, (11) alkyl halides, (12) trifluoroiodomethane, (13) Mander's reagent, and (14) chloroformates.

Alternatively, the halo-substituted heterocycle (35) can be converted to compound (3G) wherein $R^3$ is alkyl or heteroaryl via a metal (e.g., Cu or Pd) mediated coupling reaction such as, but not limited to, the Negishi reaction, the Suzuki reaction, the Sonogashira reaction, or the Stille reaction.

Scheme F

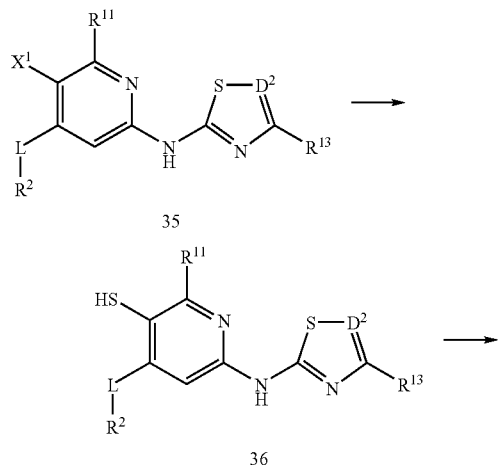

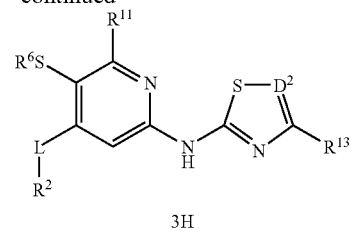

3H

Scheme F shows a method of preparing compounds (3H) of Formula I, wherein $R^3$ is $SR^6$ and $R^6$ is aryl or heteroaryl, from a halo substituted heterocycle (35). According to Scheme F, the halo-substituted heterocycle (35), prepared by the method of Scheme A or B, can be converted to a thiol or alcohol (36) via one of several procedures. According to one method, the halo-substituted heterocycle (35) is first treated with an appropriate amount of methyl lithium solution to remove exchangeable proton(s), and then transmetalated with an alkyl lithium reagent such as n-BuLi, sec-butyl or tent-butyl lithium, or a Grignard reagent such as, i-PrMg-halide. The resulting anion is then quenched with either elemental sulfur or bis(trimethylsilyl) peroxide to form the corresponding mercapto- or hydroxyl-substituted compound (36). Alternatively, the halide (35) can be converted under Pd-mediated conditions to thiol (36) utilizing potassium triisopropylsilanethiolate (*Tetrahedron Letters* (1994) 3225-3226) or sodium tert-butyldimethylsiloxide (*J. Org. Chem.*, (2002) 5553-5566). The thiol (36) can be alkylated with a variety of electrophiles using standard reaction conditions to provide the corresponding ether (3H) of Formula I. Suitable electrophiles include, but are not limited to, aryl halides and heteroaryl halides, and activated heteroaryl halides such as, but not limited to, 2-fluorocyanobenzene, 4-fluorocyanobenzene, 2-fluoronitrobenzene, 4-fluoronitrobenzene, 2-chloro-4-nitropyridine, 2-halopyridine, 2-halopyrimidine and 4-halopyrimidine.

Scheme G

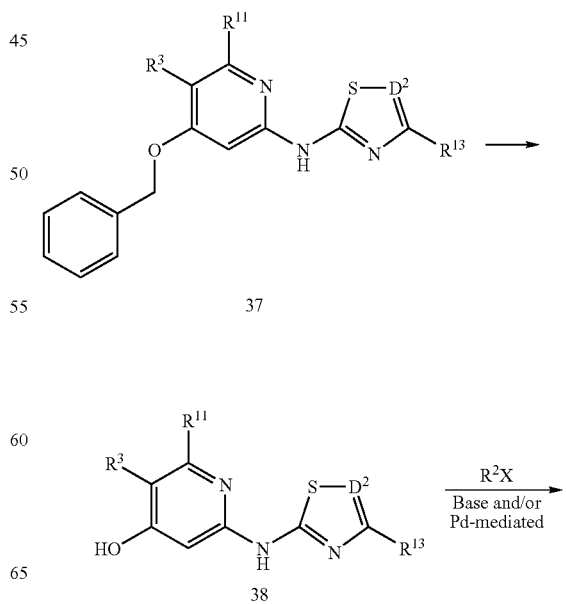

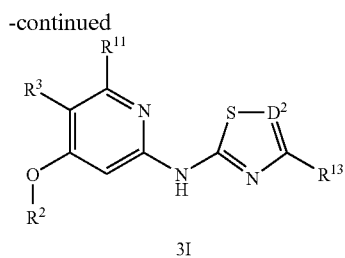

3I

Scheme G shows an alternate method of adding the linker $OR^2$ to a core heterocycle to provide a compound (3I) of Formula I. According to Scheme G, a benzyl ether (37), prepared by the method of Scheme A or B, can be converted to the hydroxyl substituted heterocycle (38), for example by hydrolysis with a strong acid (e.g., 6N HCl) or by hydrogenation (e.g., $H_2$ or ammonium formate in the presence of a metal catalyst). Reaction of the hydroxylated heterocycle (38) with $R^2X$, wherein X=F, Cl, Br, I, or $NO_2$, in the presence of a base such as, but not limited to, cesium carbonate, in a suitable solvent such as, but not limited to, DMF, affords compound (3I) of Formula I.

The method shown in Scheme G can also be used to prepare compounds of Formula I wherein L is S utilizing a paramethoxybenzyl thioether derivative of compound (37).

According to one method, substituted 2-halo-4-nitropyridine (80) (if not commercially available) can be prepared by the following sequence: Oxidation of the commercially available (or readily available from 3-bromopyridine via known methods) 3-substituted pyridine (78) by treatment with MCPBA, hydrogen peroxide or another suitable oxidant, affords the N-oxide derivative, which upon treatment with $POCl_3$, affords the pyridyl chloride (79). Oxidation of the pyridyl chloride (79), followed by treatment with nitration conditions such as nitric acid in acetic acid, followed by treatment with $PBr_3$ regioselectively affords the 2-halo-4-nitrosubstituted pyridine (80) (see *Eur. J. Org. Chem.* (2004) 3477-3488). The intermediate 3-substituted pyridine N-oxides can also be regioselectively nitrated at the 4-position with nitric acid in acetic or sulfuric acid (see *J. Org. Chem.* (1954) 1633-1640). Treatment of the pyridine N-oxide with $POCl_3$ forms the 2-halo-4-nitrosubstituted pyridine (80).

According to another method, substituted 2,4-dihalopyridine (82) can be made from 2,4-dihydroxylated pyridine (81), which is formed via a condensation reaction (e.g., for R=COOMe, see *J. Het. Chem.* (1983) 1363) by treatment with $POCl_3$ (see ester see WO 2005/028452). Alternatively, 2,4-dihalopyridine (83) can be regioselectively lithiated at low temperature and treated with an electrophile (see: *J. Org.*

Scheme H

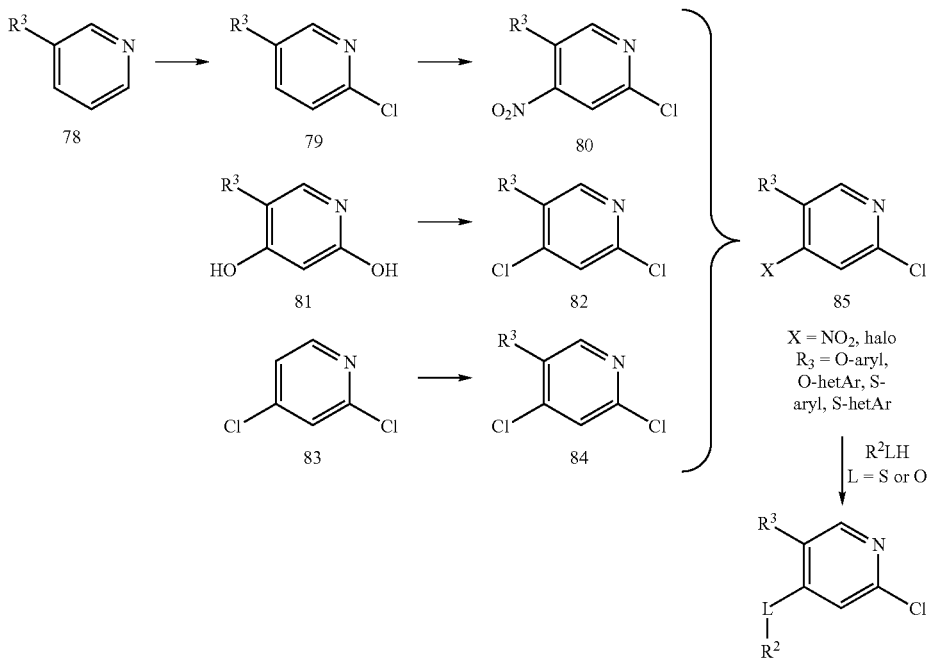

Scheme H shows several methods for preparing compound (87), which is suitable for preparing compounds of Formula I. In Scheme H, halo- or dihalosubstituted heterocycles (85) (X=$NO_2$ or halo) are reacted with a nucleophile (86) in the presence of base and a suitable solvent (e.g., NaH in DMF) to afford the halo-substituted heterocycle (87) (for similar regioselective displacement of 4-nitro-2-substituted pyridines, see *Eur J. Med. Chem.* (2004) 433-447; for similar regioselective displacement reactions of 2,4-dihalopyridines, see WO 2005/028452). Compound (85) can be prepared from compounds (80), (82) or (84), which can be made by a variety of methods.

*Chem.* (2005) 2494-2502) to provide compound (84). For example, when using bromine or iodine as the electrophile, 2,4-dichloro-5-bromopyridine or 2,4-5-iodopyridine can be prepared via this method (see *J. Org. Chem.* (2005) 2494-2502 and *Eur. J. Org Chem.* (2001) 1371-1376). The 4-Cl group of compound (84) is preferentially displaced by a nucleophiles $R^2LH$ (e.g., upon treatment with NaH in DMF). Alternatively, the 5-iodide derivative can be preferentially lithiated to form the lithium anion and be quenched with electrophiles (a two step procedure to the same compounds).

Compound (87) can be converted to a compound of Formula I by the procedure shown in Scheme A or Scheme B.

Scheme I

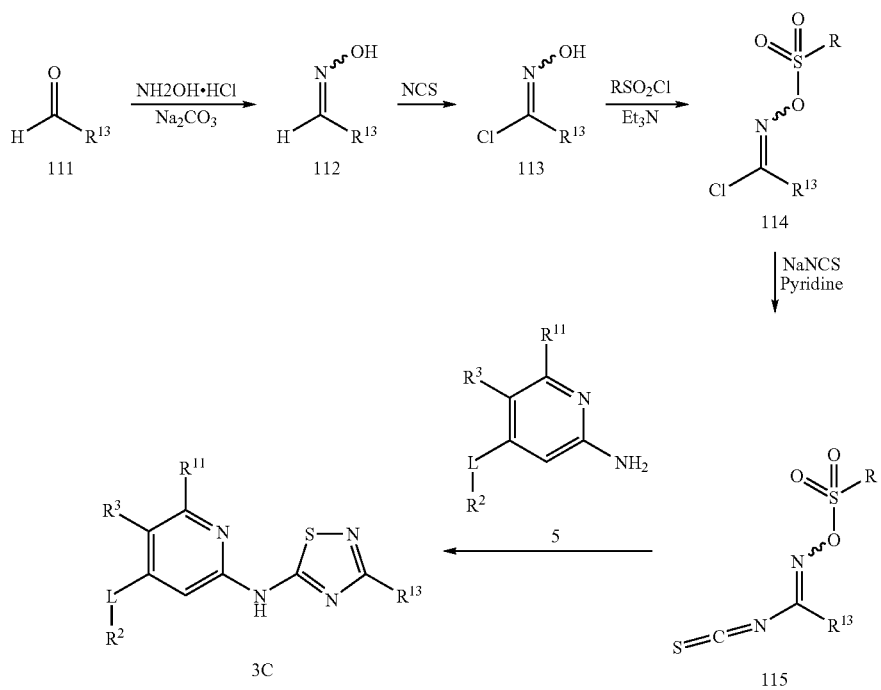

Scheme I shows an alternative method for producing compounds of the formula 3C. Formation of oxime (112) from aldehyde (111) allows for the chlorination with N-chlorosuccinimide in a suitable solvent, such as DMF, to produce (113). This product can then be sulfonylated with a sulfonyl chloride in the presence of a base, such as but not limited to triethylamine, to afford (114) (see U.S. Pat. No. 3,983,246). Reaction of (114) in a suitable solvent such as acetonitrile, with a thiocyanate salt such as NaNCS, in the presence of a base such as but not limited to pyridine, affords the activated intermediate (115) (see Takeuchi, K., JP 2001081084). This intermediate can be reacted in situ with an appropriate amino heterocycle (5) to afford compounds of the structure (3C) of Formula I.

Accordingly, another embodiment of the invention provides a method for preparing a compound of Formula I or a salt thereof, comprising:

(a) reacting a corresponding compound of the formula II

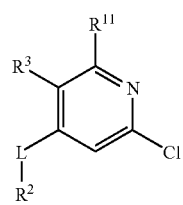

II with a corresponding compound of the formula III

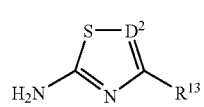

III in the presence of a base catalyst or metal catalyst; or (b) reacting a corresponding compound of the formula IV

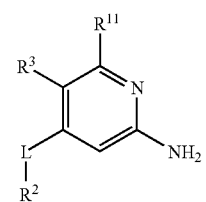

IV with a corresponding compound of the formula V

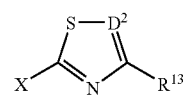

V wherein X is Cl or Br, in the presence of a base catalyst or metal catalyst; or (c) for a compound of Formula I wherein D is $CR^{12}$, reacting a corresponding compound of the formula VI

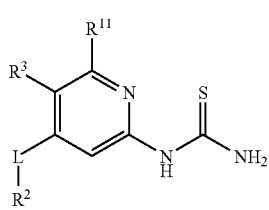

VI with a corresponding compound of the formula R¹³COCHR¹²X¹, wherein X¹ is a leaving group, in the presence of a base; or (d) for a compound of Formula I wherein R³ is SR⁶, reacting a corresponding compound having the formula VII

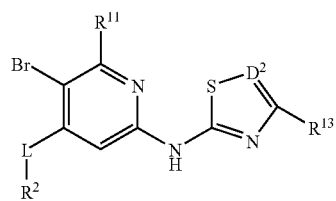

VII with a compound having the formula R⁶SSR⁶ in the presence of a suitable base; or (e) reacting a corresponding compound having the formula VIII

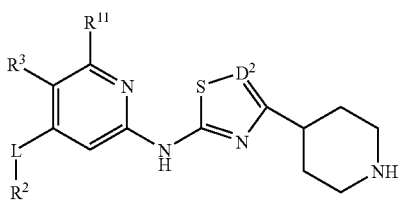

VIII with a C₁-C₆ alkyl anhydride or C₁-C₆ acid chloride in the presence of a base; or (f) reacting a corresponding compound having the formula IX

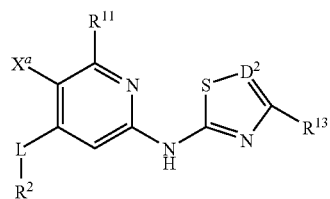

IX wherein Xᵃ is a leaving atom, with a compound having the formula R³—Xᵇ wherein Xᵇ is a leaving atom or a leaving group, in the presence of a suitable base; or (g) for a compound wherein R³ is SR⁶ and R⁶ is aryl or heteroaryl, reacting a corresponding compound having the formula X

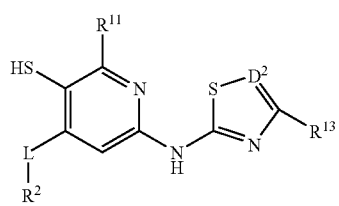

X with a compound having the formula R⁶—Xᶜ, wherein Xᶜ is a leaving atom or group, in the presence of a suitable base; or (h) for a compound of Formula I wherein L is O or S, reacting a corresponding compound having the formula XI

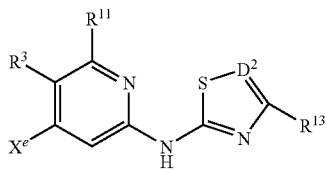

XI wherein Xᵉ is a leaving group or atom, with a compound having the formula R²LH wherein L is O or S, in the presence of a palladium catalyst and a suitable base; or (i) for a compound of Formula I wherein D² is N, reacting a corresponding compound of the formula XII

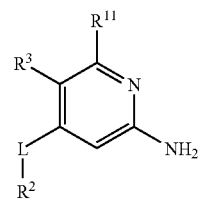

XII with a compound having the formula XIII

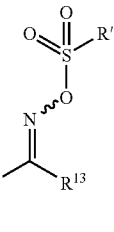

XIII where R' is C₁-C₆ alkyl or aryl optionally substituted with C₁-C₆ alkyl, in the presence of a base; or (j) for a compound of Formula I wherein L is O or S, reacting a corresponding compound of the formula XIV

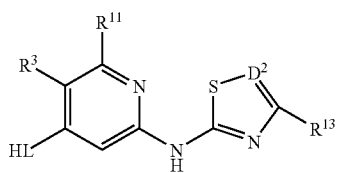

XIV with a compound having the formula R²—Xᵍ, wherein Xᵍ is a leaving atom or group, in the presence of a base; and
removing any protecting groups and, if desired, forming a salt.

Referring to method (b), X can be a leaving atom (for example, Cl, Br) or a leaving group (e.g., OTs or OTf).

Referring to step (c), examples of suitable leaving groups include OTs, Cl, Br, I, and N(1-6C alkyl)₃.

Referring to step (d), a suitable base may be, for example, an alkyl lithium base such as methyl lithium, butyl lithium, or a mixture thereof.

Referring to step (e), a suitable base includes a tertiary amine base, for example, pyridine or triethylamine.

Referring to step (f), $X^a$ may be a leaving atom such as a halogen, such as Br, Cl or I, and $X^b$ may be a leaving atom such as a halogen (e.g., F, Cl or Br) or a leaving group such as a sulfonate (e.g., OMs or OTs). A suitable base may be, for example, an alkyl lithium such as methyl lithium, butyl lithium, or a combination thereof.

Referring to step (g), $X^c$ may be a leaving atom such as a halogen (e.g., F, Cl or Br) or a leaving group such as a sulfonate (e.g., OMs or OTs).

Referring to step (h), $X^e$ may be a leaving group such as a sulfonate (e.g., OMs or OTs), or a leaving atom such as a halogen (e.g., Br, I). Suitable palladium catalysts include $Pd(OAc)_2$ and a suitable ligand. Suitable bases include alkali metal carbonates, hydrides, or alkoxides, such as $Na_2CO_3$, $K_2CO_3$, NaH, and NaOt-Bu. Suitable solvents include toluene. The reaction is conveniently performed at temperatures ranging from ambient temperature to 100° C.

Referring to step (i), a suitable base includes a tertiary amine base such as pyridine.

Referring to step (j), the leaving atom or group can be, for example, F, Cl, Br, I or $NO_2$. A suitable base includes an alkali metal carbonate such as $CsCO_3$.

Compounds of formula VIII

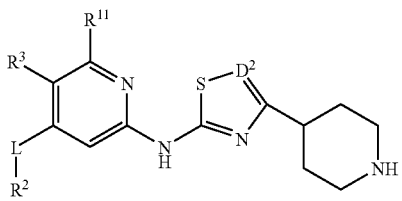

VIII wherein $R^2$, $R^3$, $R^{11}$ and $D^2$ are as defined for Formula I, are also believed to be novel and are further provided as part of this invention. Compounds of Formula VIII may be glucokinase activators and are further useful for preparing compound of Formula I.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991. Suitable carboxyl protecting group include any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl.

The compounds of the present invention are useful as prophylactics or therapeutic agents for treating diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed below. Furthermore, the compounds of the present invention can be also used to prevent the progression of the borderline type, impaired glucose tolerance, IFG (impaired fasting glucose) or IFG (impaired fasting glycemia) to diabetes mellitus.

Accordingly, another aspect of the invention provides methods of treating or preventing diseases or conditions described herein by administering to a mammal, such as a human, a therapeutically effective amount of a compound of Formula I in an amount effective to treat or prevent said disorder.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

The terms "treat" and "treatment" refer to both therapeutic treatment and prophylactic or preventative measures, wherein the object is to prevent or slow down (lessen) an undesired physiological change or disorder.

As used herein, the term "mammal" refers to a warm-blooded animal that has or is at risk of developing a disease described herein and includes, but is not limited to, guinea pigs, dogs, cats, rats, mice, hamsters, and primates, including humans.

An additional aspect of the invention is the use of a compound of Formula I in the preparation of a medicament for therapy, such as for the treatment or prevention diseases or disorders mediated by deficient levels of glucokinase activity or which can be treated by activating glucokinase.

This invention also provides compounds of Formula I for use in the treatment of diseases or disorders mediated by deficient levels of glucokinase activity or which can be treated by activating glucokinase.

The compounds of the present invention can be used in combination with one or more additional drugs, for example a compound that works by a different mechanism of action, such as insulin preparations, agents for improving insulin resistance, alpha-glucosidase inhibitors, biguanides, insulin secretagogues, dipeptidylpeptidase IV inhibitors, beta-3 agonists, amylin agonists, phosphotyrosine phosphatase inhibitors, gluconeogenesis inhibitors, sodium-glucose cotransporter inhibitors, known therapeutic agents for diabetic complications, antihyperlipidemic agents, hypotensive agents, antiobesity agents.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of formula (I) or a pharmaceutically acceptable salt thereof, as defined hereinabove. In one embodiment, the pharmaceutical composition includes the compound of formula (I) together with a pharmaceutically acceptable diluent or carrier.

EXAMPLES

The following examples illustrate the invention. Accordingly, the compounds of this invention also include the compounds of Examples 1-19, with the exception of compounds labeled as "representative examples". The representative examples were found to be weakly active in the assays described herein, and are provided to illustrate synthetic routes to compounds of the invention or to describe intermediates useful in the synthesis of compounds of this invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters). $^1$H NMR spectra were recorded on a Varian instrument operating at 400 MHz. $^1$H-NMR spectra were obtained, for example, as CDCl$_3$ or d$_6$-DMSO solutions (reported in ppm), using (7.25 ppm) or tetramethylsilane (0.00 ppm) as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

3-(2-(4-(1-Acetylpiperidin-4-yl)thiazol-2-ylamino) pyridin-4-yloxy)isonicotinonitrile hydrochloride

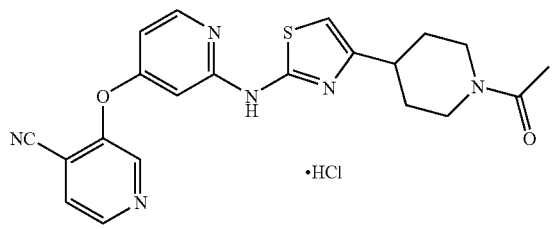

Step A: Preparation of 1-acetyl-N-methoxy-N-methylpiperidine-4-carboxamide: To a solution of 1-acetylpiperidine-4-carboxylic acid (58.50 g, 341.7 mmol) in dichloromethane (700 mL) was added di(1H-imidazol-1-yl)methanone (58.18 g, 358.8 mmol) in portions. The mixture was agitated for two hours and N-methoxymethanamine hydrochloride (35.00 g, 358.8 mmol) was added at once. The mixture was stirred overnight at ambient temperature, and then 4M HCl in dioxane (75 mL) was added slowly. The slurry was agitated for 30 minutes and then filtered. The filtrate was washed twice with sodium bicarbonate solution, dried and concentrated in vacuo to give the desired product (59.10 g, 80.72% yield) as a white solid.

Step B: Preparation of 1,1'-(piperidine-1,4-diyl)diethanone: 1-Acetyl-N-methoxy-N-methylpiperidine-4-carboxamide (59.10 g, 275.8 mmol) was dissolved in tetrahydrofuran (800 mL) and cooled to 0° C. Methylmagnesium bromide (110.3 mL, 331.0 mmol) (3.0 M in diethyl ether) was added slowly and the resulting white slurry was agitated for 1 hour. The reaction was quenched with 300 ml of 2M HCl and organic solvent was evaporated. The resulting aqueous slurry was extracted three times with 20:80 isopropanol/chloroform. The resulting extracts were washed with brine and evaporated to produce the desired product (38.40 g, 82.27% yield) as amber oil.

Step C: Preparation of 1-(1-acetylpiperidin-4-yl)-2-bromoethanone: 1,1'-(Piperidine-1,4-diyl)diethanone (38.00 g, 224.6 mmol) was dissolved in methanol (700 mL) and bromine (12.11 mL, 235.8 mmol) was added in portions. The resulting mixture was agitated 3 hours and the solvent was removed in vacuo. The resulting solid was triturated with ethyl acetate and partitioned between ethyl acetate and sodium carbonate solution. The organic phase was separated, washed with brine, dried and evaporated to give the desired product (44.70 g, 80.23% yield) as yellow solid.

Step D: Preparation of 1-(4-(2-aminothiazol-4-yl)piperidin-1-yl)ethanone: 1-(1-acetylpiperidin-4-yl)-2-bromoethanone (2.37 g, 9.561 mmol) and thiourea (0.728 g, 9.561 mmol) were dissolved in ethanol (40 mL) and agitated at ambient temperature for 30 minutes. The mixture was heated to 80° C. and agitated an additional 1 hour. Upon cooling solvent was evaporated and the residue was distributed between 20 mL of 2M NaOH and 20 mL of chloroform. The organic phase was separated and discarded. The remaining aqueous phase (white slurry) was extracted with chloroform until all solids were extracted (4×200 mL). The organic extracts were combined, dried over magnesium sulfate and evaporated to give the desired product (1.600 g, 74.27% yield) as white solid.

Step E: Preparation of 3-(2-(4-(1-acetylpiperidin-4-yl) thiazol-2-ylamino)pyridin-4-yloxy)isonicotinonitrile hydrochloride: 3-(2-Chloropyridin-4-yloxy)isonicotinonitrile (0.0650 g, 0.281 mmol) (prepared as in Example 2), 1-(4-(2-aminothiazol-4-yl)piperidin-1-yl)ethanone (0.0822 g, 0.365 mmol), potassium phosphate (0.137 g, 0.421 mmol), tris(dibenzylideneacetone)dipalladium (0) (0.00642 g, 0.00701 mmol) and 9,9-dimethyl-4,5-bis(diphenylphosphino)xanthene (0.00812 g, 0.0140 mmol) were combined and the vessel was capped with rubber septum. The vessel was evacuated and purged with nitrogen three times. Toluene (2 mL) and degassed water (2 mL) were added and the resulting mixture was heated to 90° C. and agitated overnight. After cooling the mixture was diluted with 50 ml of ethyl acetate and washed with sodium bicarbonate, brine, dried and evaporated. The crude product was purified by preparative HPLC (Parallex) and converted to HCl salt by treatment with 2M HCl in ether to provide the title compound (0.0150 g, 12.71% yield) as white solid. $^1$H NMR (CDCl$_3$) δ 1.52-1.62 (m, 2H), 1.98-2.06 (m, 2H), 2.10 (s, 3H), 2.65 (t, 1H), 2.80 (t, 1H), 3.13 (t, 1H), 3.85 (d, 1H), 4.66 (d, 1H), 6.35 (s, 1H), 6.45 (s, 1H), 6.50 (d, 1H), 7.15 (s, 1H), 7.40 (d, 1H), 8.05 (s, 1H), 9.01 (bs, 1H).

Example 2 (Representative Example)

3-(2-chloropyridin-4-yloxy)isonicotinonitrile

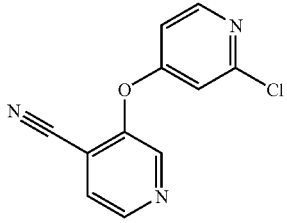 [SMILES: N#Cc1ccncc1Oc1ccnc(Cl)c1]

Step A: Preparation of 3-chloroisonicotinonitrile: In a 4 neck 3 L round bottom flask equipped with mechanical stirrer and condenser, was added 4-cyanopyridine-n-oxide (50 g, 416 mmol), phosphoryl trichloride (153 ml, 1665 mmol), and phosphorous pentachloride (121 g, 583 mmol). The reaction was stirred at 105° C. overnight. The reaction mixture was cooled and then slowly added in portions to 2 kg ice. The pH was adjusted to about 8 by slow addition of 50% NaOH. The mixture was extracted with ethyl acetate. The organic layer was dried and concentrated. The residue was purified by silica gel chromatography, eluting with 5-10% ethyl acetate to give the desired product (23 g, 39.9% yield) as light yellow solid.

Step B: Preparation of 3-(2-(trimethylsilyl)ethoxy)isonicotinonitrile: A flask was charged with 2-(trimethylsilyl)ethanol (1.02 g, 8.66 mmol) and added THF (20 mL). Sodium hydride (0.219 g, 8.66 mmol) was added and the reaction was stirred at ambient temperature for 1 hour. 3-Chloroisonicotinonitrile (1.00 g, 7.22 mmol) was added, and the reaction mixture was stirred at ambient temperature for 1 hour and then at 50° C. overnight. A saturated solution of ammonium chloride was added. The reaction mixture was extracted with ethyl acetate, dried and concentrated to give the desired product (1.30 g, 81.7% yield) as light brown semi solid material.

Step C: Preparation of 3-hydroxyisonicotinonitrile: A flask was charged with 3-(2-(trimethylsilyl)ethoxy)isonicotinonitrile (1.30 g, 5.90 mmol), THF (5 mL) and N,N-dibutyl-N-propylbutan-1-aminium fluoride (11.8 mL, 11.8 mmol) in THF was added. The reaction mixture was stirred at ambient temperature for 1 hour and then concentrated. The crude product was purified by silica gel chromatography, eluting with DCM and 5% methanol in DCM to give the desired product (0.7 g, 99% yield) as dark brown oil.

Step D: Preparation of 3-(2-chloropyridin-4-yloxy)isonicotinonitrile: A flask was charged with sodium hydride (3.99 g, 158 mmol) and DMF (50 mL), and 3-hydroxyisonicotinonitrile (15.8 g, 132 mmol) was added. The reaction was stirred for 2 hours at ambient temperature. 2-Chloro-4-nitropyridine (21.9 g, 138 mmol) was added and the reaction was and stirred overnight. Water was added and the reaction was extracted with ethyl acetate. The organic layer was dried and concentrated. The crude product was purified by silica gel chromatography, eluting with DCM, 5% ammoniated methanol in DCM to give the desired product (0.250 g, 0.820% yield) as yellow solid.

Example 3

1-(4-(2-(4-(2,6-Dichlorophenylthio)pyridin-2-ylamino)thiazol-4-yl)piperidin-1-yl)ethanone hydrochloride

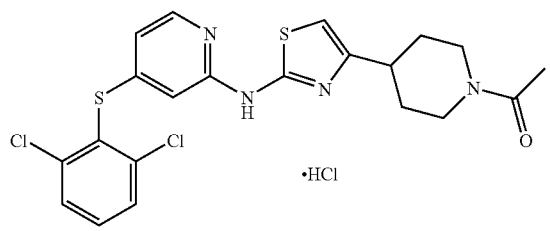 [SMILES: CC(=O)N1CCC(c2csc(Nc3cc(Sc4c(Cl)cccc4Cl)ccn3)n2)CC1 ; Cl]

Prepared according to the method of Example 1, Step E. $^1$H NMR (CDCl$_3$) δ 1.52-1.62 (m, 2H), 1.98-2.06 (m, 2H), 2.10 (s, 3H), 2.65 (t, 1H), 2.80 (t, 1H), 3.13 (t, 1H), 3.85(d, 1H), 4.66 (d, 1H), 6.35 (s, 1H), 6.45 (s, 1H), 6.50 (d, 1H), 7.34 (t, 1H), 7.50 (d, 1H), 8.10 (d, 1H), 9.01 (bs, 1H).

Example 4

1-(4-(2-(4-(2-cChlorophenoxy)pyridin-2-ylamino)thiazol-4-yl)piperidin-1-yl)ethanone hydrochloride

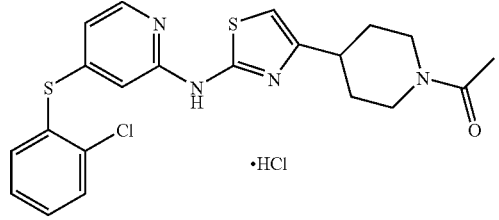 [SMILES: CC(=O)N1CCC(c2csc(Nc3cc(Sc4ccccc4Cl)ccn3)n2)CC1 ; Cl]

Prepared according to the method of Example 1, Step E. $^1$H NMR (CDCl$_3$) δ 1.52-1.62 (m, 2H), 1.98-2.06 (m, 2H), 2.10 (s, 3H), 2.65 (t, 1H), 2.80 (t, 1H), 3.13 (t, 1H), 3.85(d, 1H), 4.66 (d, 1H), 6.35 (s, 1H), 6.45-6.47 (m, 2H), 7.16-7.52 (m, 4H), 8.18 (d, 1H), 8.91 (bs, 1H).

Example 5

1-(4-(2-(4-(2,6-Dimethylphenoxy)pyridin-2-ylamino)thiazol-4-yl)piperidin-1-yl)ethanone hydrochloride

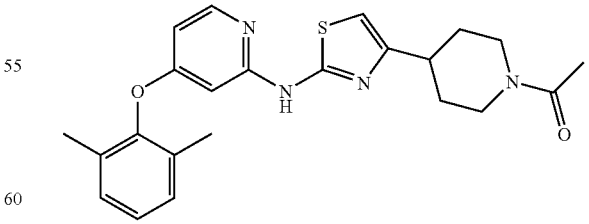

Prepared according to the method of Example 1, Step E. $^1$H NMR (CDCl$_3$) 1.52-1.62 (m, 2H), 1.98-2.06 (m, 2H), 2.10 (s, 3H), 2.12 (s, 6H) 2.65 (t, 1H), 2.80 (t, 1H), 3.13 (t, 1H), 3.85(d, 1H), 4.66 (d, 1H), 6.25 (s, 1H), 6.35 (s, 1H), 6.42 (d, 1H), 7.11 (d, 2H), 7.34-7.45 (m, 2H), 8.18 (m, 2H).

Example 6

1-(4-(2-(4-(2-Chloro-6-methylphenoxy)pyridin-2-ylamino)thiazol-4-yl)piperidin-1-yl)ethanone hydrochloride

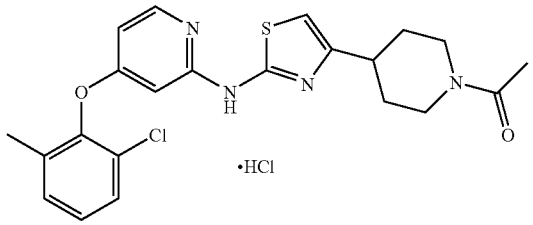 [SMILES: CC(=O)N1CCC(c2csc(Nc3cc(Oc4c(C)cccc4Cl)ccn3)n2)CC1 ; Cl]

Prepared according to the method of Example 1, Step E. $^1$H NMR (CDCl$_3$) δ 1.52-1.62 (m, 2H), 1.98-2.06 (m, 2H), 2.10 (s, 3H), 2.15 (s, 3H), 2.65 (t, 1H), 2.80 (t, 1H), 3.13 (t, 1H), 3.85(d, 1H), 4.66 (d, 1H), 6.35 (s, 1H), 6.45 (s, 1H), 6.50 (d, 1H), 7.34 (t, 1H), 7.50 (d, 1H), 8.10 (d, 1H), 9.01 (bs, 1H).

Example 7 (Representative Example)

Ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate

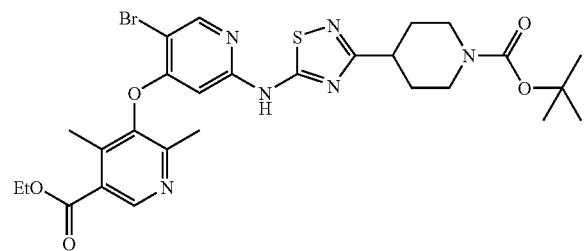 [SMILES: CCOC(=O)c1cnc(C)c(Oc2cc(Nc3nc(C4CCN(C(=O)OC(C)(C)C)CC4)ns3)ncc2Br)c1C]

Step A: Preparation of (5-(2-chloropyridin-4-yloxy)-4,6-dimethylpyridin-3-yl)methanol: A suspension of sodium hydride (5.27 g, 209 mmol) in DMF (100 mL) was carefully charged with 5-(hydroxymethyl)-2,4-dimethylpyridin-3-ol hydrochloride (18 g, 95 mmol). The mixture stirred at ambient temperature for 2 hours. 2-chloro-4-nitropyridine (15 g, 95 mmol) was then added and the reaction stirred overnight at ambient temperature. The material was diluted with water and extracted with ethyl acetate. The organic layer was dried, and concentrated. Flash chromatography (dichloromethane/methanol 20:1) gave the title compound (19.8 g, 79%) as colorless oil.

Step B: Preparation of 5-(2-chloropyridin-4-yloxy)-4,6-dimethylnicotinic acid: (5-(2-chloropyridin-4-yloxy)-4,6-dimethylpyridin-3-yl)methanol (5.00 g, 18.9 mmol) was charged with NaOH (0.1N in H$_2$0, 19 ml, 1.9 mmol). Aqueous KMnO$_4$ (3%, 119 mL, 22.7 mmol) was then added. The reaction stirred at ambient temperature overnight. The solution was diluted with dichloromethane, filtered through celite, and acidified with citric acid. The organic layer was separated and the aqueous layer was extracted with DCM. The combined organic layers were dried and concentrated to give the title compound (2.66 g, 51%).

Step C: Preparation of ethyl 5-(2-chloropyridin-4-yloxy)-4,6-dimethylnicotinate: A three necked round bottom flask containing 5-(2-chloropyridin-4-yloxy)-4,6-dimethylnicotinic acid (11.7 g, 42.0 mmol) was charged with ethanol (250 mL), benzene (300 mL) and sulphuric acid (10 mL). The flask was fitted with Dean Stark apparatus and the reaction stirred at reflux overnight. The solution was cooled and carefully neutralized with saturated NaHCO$_3$ solution. The material was extracted with EtOAc, dried, and concentrated to afford the title compound (8.6 g, 67%) as an oil which solidified to a white solid upon standing in a refrigerator (4° C.) overnight.

Step D: Preparation of ethyl 5-(2-aminopyridin-4-yloxy)-4,6-dimethylnicotinate: A round bottom flask containing ethyl 5-(2-chloropyridin-4-yloxy)-4,6-dimethylnicotinate (7.5 g, 25 mmol), tert-butyl carbamate (8.6 g, 73 mmol), potassium phosphate (tribasic) (5.7 g, 27 mmol), tris(dibenzylideneacetone)dipalladium (1.1 g, 1.2 mmol), and 9,9-dimethyl-4,5-bis(diphenylphosphino)xanthene (1.1 g, 1.8 mmol) was suspended in toluene (200 mL) and water (40 mL). The solution was degassed with nitrogen and then stirred at 90 C for 4 hours. The solution was filtered through GF/F paper and diluted with water. The material was then extracted with EtOAc and the organic layer was dried, and concentrated. The residue was then slowly diluted in TFA (50 mL) and stirred at ambient temperature for 6 hours. The solution was concentrated, diluted with water, and neutralized with saturated NaHCO$_3$ solution. The material was extracted with EtOAc and the organic layer was dried, and concentrated. Flash chromatography of the residue (10% MeOH/EtOAc) gave the title compound (3.8 g, 54%).

Step E: Preparation of ethyl 5-(2-amino-5-bromopyridin-4-yloxy)-4,6-dimethylnicotinate: Ethyl 5-(2-aminopyridin-4-yloxy)-4,6-dimethylnicotinate (2.5 g, 8.7 mmol) in AcOH (30 mL) was charged with dropwise addition of bromine (1M in AcOH, 8.7 ml, 8.7 mmol). The solution was stirred at ambient temperature for 30 minutes. The solution was then concentrated and neutralized with saturated NaHCO$_3$ solution. The material was then extracted with EtOAc and the organic layer was dried, and concentrated. Flash chromatography gave the title compound (1.88 g, 59%) as a yellow solid.

Step F: Preparation of tert-butyl 4-((hydroxyimino)methyl)piperidine-1-carboxylate: A mixture of tert-Butyl 4-formylpiperidine-1-carboxylate (30.0 g, 140 mmol), MeOH (150 mL, 3700 mmol) and water (150 mL, 8330 mmol) was cooled in an ice-water bath. Hydroxylamine hydrochloride (11.7 g, 160 mmol) and sodium carbonate (7.45 g, 70 mmol) were added and the resulting mixture was stirred in the ice bath, then allowed to warm to ambient temperature overnight. The reaction was concentrated to an aqueous suspension and was extracted with ethyl acetate. The organic extract was washed with brine, dried, and concentrated to afford the title compound as a white solid (31.3 g, 98%).

Step G: Preparation of tert-butyl 4-(chloro(hydroxyimino)methyl)piperidine-1-carboxylate: tert-Butyl 4-((hydroxyimino)methyl)piperidine-1-carboxylate (2.0 g, 8.8 mmol) in DMF (100 mL) was charged with 1-chloropyrrolidine-2,5-dione (1.2 g, 8.8 mmol). The reaction stirred at ambient temperature overnight. The material was poured into a 1:1 brine:water mixture and the resultant solution was extracted with ethyl acetate. The organic layer was wash twice with water, dried, and concentrated to afford the title compound (2.3 g, 100%).

Step H: Preparation of tert-butyl 4-(chloro(methylsulfonyloxyimino)methyl)piperidine-1-carboxylate: tert-Butyl 4-(chloro(hydroxyimino)methyl)piperidine-1-carboxylate (2.3 g, 8.75 mmol) and methanesulfonyl chloride (0.68 mL, 8.75 mmol) were suspended in diethyl ether (200 mL). Triethylamine (1.22 mL, 8.75 mmol) was added and the reaction stirred at ambient temperature until consumption of starting material. The mixture was filtered and the filtrate was concentrated. The residue was purified by flash chromatography (using dichloromethane) to afford the title compound (1.6 g, 53% yield) as a clear oil.

Step I: Preparation of ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate: tert-Butyl 4-(Chloro (methylsulfonyloxyimino)methyl)piperidine-1-carboxylate (2.57 g, 7.5 mmol, was dissolved in acetonitrile (50 mL). Pyridine (1.8 ml, 23 mmol) and NaSCN (0.61 g, 7.5 mmol) were then added and the reaction stirred at 40° C. for 40 minutes. Ethyl 5-(2-amino-5-bromopyridin-4-yloxy)-4,6-dimethylnicotinate (1.84 g, 5.0 mmol) was then added and the reaction stirred at 60° C. overnight. The solution was then cooled and quenched with saturated NaHCO₃ solution. The material was extracted with EtOAc and the organic layer was dried and concentrated. Flash chromatography of the residue gave the title compound (2.53 g, 80% yield) as a yellow solid. ¹H NMR (400 MHz, CDCl₃) δ 1.44 (s, 9H), 1.44 (t, 3H), 1.72-1.79 (m, 2H), 1.96-1.99 (m, 2H), 2.41 (s, 3H), 2.43 (s, 3H), 2.85-2.92 (m, 3H), 4.07-4.13 (m, 2H), 4.42 (q, 2H), 5.79 (s, 1H), 8.55 (s, 1H), 8.90 (s, 1H).

Example 8 (Representative Example)

5-(2-(3-(1-(tert-butoxycarbonyl)piperidin-4-yl)-1,2,4-thiadiazol-5-ylamino)-5-bromopyridin-4-yloxy)-4,6-dimethylnicotinic acid

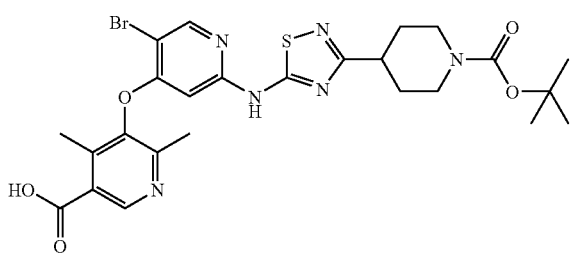 [SMILES: Cc1ncc(C(=O)O)c(C)c1Oc1cc(Nc2nc(C3CCN(C(=O)OC(C)(C)C)CC3)ns2)ncc1Br]

Ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate (prepared according to Example 7; 0.050 g, 0.08 mmol) was dissolved in EtOH (2 mL). NaOH (1N in H₂O, 0.28 ml, 0.28 mmol) was added. The reaction stirred at 60° C. for 1 hour. The solution was cooled and concentrated. The material was acidified with saturated NH₄Cl solution and extracted with dichloromethane. The organic layer was washed with water, dried and concentrated to give 5-(2-(3-(1-(tert-butoxycarbonyl)piperidin-4-yl)-1,2,4-thiadiazol-5-ylamino)-5-bromopyridin-4-yloxy)-4,6-dimethylnicotinic acid (0.012 g, 25% yield) as an off white solid. ¹H NMR (400 MHz, DMSO-d₆) δ 1.39 (s, 9H), 1.52-1.55 (m 2H), 1.89-1.93 (m, 2H), 2.34 (s, 6H), 2.84-2.93 (m, 3H), 3.90-3.94 (m, 2H), 6.20 (s, 1H), 8.62 (s, 1H), 8.89 (s, 1H), 11.69 (s, 1H), 13.09 (s, 1H).

Example 9 (Representative Example)

tert-Butyl 4-(5-(4-(5((2-(dimethylamino)ethyl)carbamoyl)-2,4-dimethylpyridin-3-yloxy)-5-bromopyridin-2-ylamino)-1,2,4-thiadiazol-3-yl)piperidine-1-carboxylate

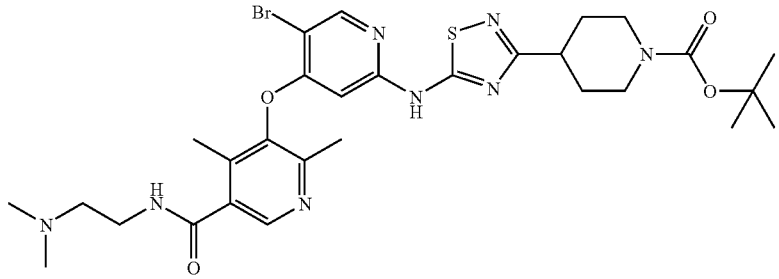 [SMILES: Cc1ncc(C(=O)NCCN(C)C)c(C)c1Oc1cc(Nc2nc(C3CCN(C(=O)OC(C)(C)C)CC3)ns2)ncc1Br]

Ethyl 5-(2-(3-(1-(tert-butoxycarbonyl)piperidin-4-yl)-1,2,4-thiadiazol-5-ylamino)-5-bromopyridin-4-yloxy)-4,6-dimethylnicotinate (prepared according to Example 7; 0.50 g, 0.79 mmol) was dissolved in EtOH (10 mL). NaOH (1N in H₂O, 2.0 ml, 2.0 mmol) was added. The reaction stirred at 60° C. for 3 hours. The solution was cooled and concentrated to give the hydrolyzed product as a yellow salt. This residue was re-dissolved in DMF (2 mL). N1,N1-dimethylethane-1,2-diamine (0.31 mL, 2.8 mmol), 1-[3-(dimethylamino)propyl]-3-ethylcarbodiimide hydrochloride (0.45 g, 2.4 mmol) and HOBT.H₂O (0.36 g, 2.4 mmol) were added. The reaction stirred at 50° C. for 2 hours. The solution was cooled, diluted with water (15 mL), extracted with EtOAc, dried, and concentrated. Flash chromatography (DCM-15% MeOH/DCM/ 0.1-1% NH₄OH) gave the title compound (0.30 g, 56%) as an off-white solid. ¹H NMR (400 MHz, CDCl₃) δ 1.45 (s, 9H), 1.70-1.77 (m, 2H), 1.95-1.99 (m, 2H), 2.25 (s, 3H), 2.29 (s, 6H), 2.39 (s, 3H), 2.56-2.62 (m, 2H), 2.85-2.89 (m 3H), 3.52-2.64 (m, 2H), 4.08-4.15 (m, 2H), 5.95 (s, 1H), 7.07 (s, 1H), 8.30 (s, 1H), 8.53 (s, 1H), 10.15 (s, 1H).

Example 10 (Representative Example)

5-(5-Bromo-2-(3-(piperidin-4-yl)-1,2,4-thiadiazol-5-ylamino)pyridin-4-yloxy)-N-(2-(dimethylamino) ethyl)-4,6-dimethylnicotinamide dihydrochloride

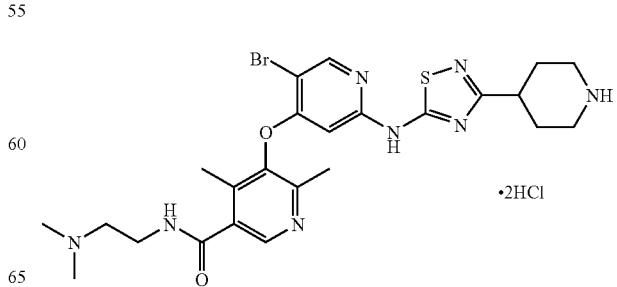

tert-Butyl 4-(5-(4-(5-((2-(dimethylamino)ethyl)carbamoyl)-2,4-dimethylpyridin-3-yloxy)-5-bromopyridin-2-ylamino)-1,2,4-thiadiazol-3-yl)piperidine-1-carboxylate (prepared according to Example 9; 0.025 g, 0.037 mmol) was dissolved in a mixture of methanol:dichloromethane (1 mL each). HCl (4N in dioxane, 0.5 mL, 2.0 mmol) was added. The reaction stirred overnight. The solution was concentrated to give 5-(5-bromo-2-(3-(piperidin-4-yl)-1,2,4-thiadiazol-5-ylamino)pyridin-4-yloxy)-N-(2-(dimethylamino)ethyl)-4,6-dimethylnicotinamide dihydrochloride (0.028 g, 100% yield) as an off-white solid. $^1$H NMR (400 MHz, DMSO-d$_6$) δ 1.87-1.93 (m, 2H), 2.06-2.14 (m, 2H), 2.22 (s, 3H), 2.34 (s, 3H), 2.83 (s, 3H), 2.84 (s, 3H), 2.96-3.08 (m, 2H), 3.23-3.32 (m, 4H), 3.44-2.52 (m, 1H), 3.62-3.73 (m, 2H), 6.37 (s, 1H), 8.64 (s, 1H), 8.67 (s, 1H), 8.70 (s, 1H), 9.0 (s, 1H), 9.03 (t, 1H), 10.50 (s, 1H), 11.88 (s, 1H).

Example 11 (Representative Example)

tert-Butyl 4-(5-(5-bromo-4-(2-chloro-5-((2-(dimethylamino)ethyl)carbamoyl)phenoxy)pyridin-2-ylamino)-1,2,4-thiadiazol-3-yl)piperidine-1-carboxylate

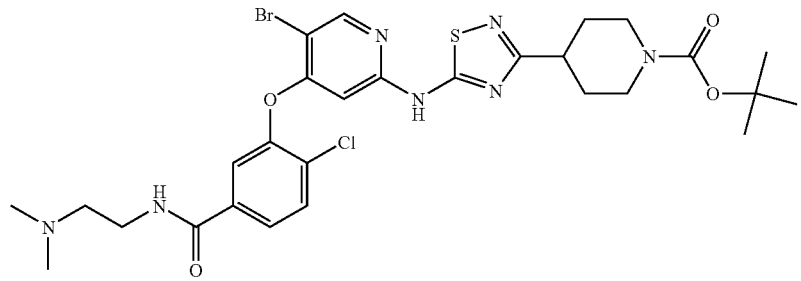 [SMILES: CN(C)CCNC(=O)c1ccc(Cl)c(Oc2cc(Nc3nc(C4CCN(C(=O)OC(C)(C)C)CC4)ns3)ncc2Br)c1]

Prepared from ethyl 3-(2-amino-5-bromopyridin-4-yloxy)-4-chlorobenzoate according to the method of Example 7 (step I) and Example 9. $^1$H NMR (400 MHz, CDCl$_3$) δ 1.45 (s, 9H), 1.69-1.76 (m, 2H), 1.94-1.97 (m, 2H), 2.20 (s, 6H), 2.57 (t, 2H), 2.82-2.89 (m, 3H), 3.54-3.58 (m, 2H), 4.07-4.11 (m, 2H), 5.95 (s, 1H), 7.39 (s, 1H), 7.52 (d, 1H), 7.54 (s, 1H), 7.62 (dd, 1H), 8.48 (s, 1H).

Example 12 (Representative Example)

3-(5-Bromo-2-(3-(piperidin-4-yl)-1,2,4-thiadiazol-5-ylamino)pyridin-4-yloxy)-4-chloro-N-(2-(dimethylamino)ethyl)benzamide dihydrochloride

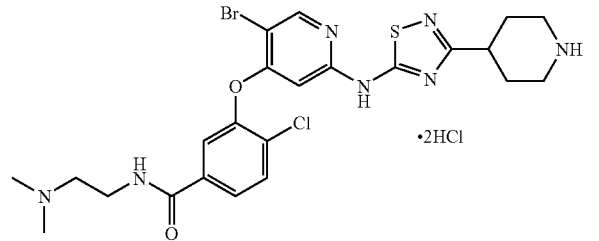 [SMILES: CN(C)CCNC(=O)c1ccc(Cl)c(Oc2cc(Nc3nc(C4CCNCC4)ns3)ncc2Br)c1 ; "·2HCl"]

Prepared from tert-butyl 4-(5-(5-bromo-4-(2-chloro-5-((2-(dimethylamino)ethyl)carbamoyl)phenoxy)pyridin-2-ylamino)-1,2,4-thiadiazol-3-yl)piperidine-1-carboxylate according to the method of Example 10. $^1$H NMR (400 MHz, DMSO-d$_6$) δ 1.88-1.92 (m, 2H), 2.08-2.14 (m, 2H), 2.81 (s, 3H), 2.82 (s, 3H), 2.96-3.16 (m, 2H), 3.24-3.32 (m, 4H), 3.44-3.52 (m, 1H), 3.61-3.72 (m, 2H), 6.44 (s, 1H), 7.89 (d, 1H), 7.98 (d, 1H), 7.98 (s, 1H), 8.64 (s, 1H), 8.70 (s, 1H), 8.85 (s, 1H), 9.05 (s, 1H), 10.10 (s, 1H), 11.95 (s, 1H).

Example 13

3-(2-(3-(1-Acetylpiperidin-4-yl)-1,2,4-thiadiazol-5-ylamino)-5-bromopyridin-4-yloxy)-4-chloro-N-(2-(dimethylamino)ethyl)benzamide

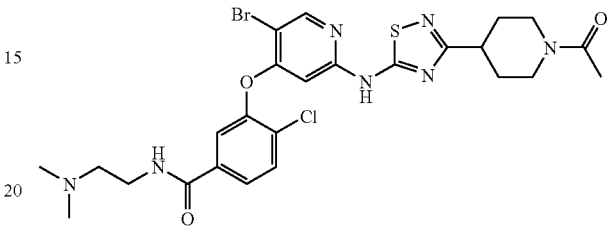

3-(5-Bromo-2-(3-(piperidin-4-yl)-1,2,4-thiadiazol-5-ylamino)pyridin-4-yloxy)-4-chloro-N-(2-(dimethylamino)ethyl)benzamide dihydrochloride (0.12 g, 0.18 mmol) was dissolved in DMF (2 mL) and the solution was cooled to 0° C. DIEA (0.13 mL, 0.73 mmol) was added followed by acetyl chloride (0.017 mL, 0.24 mmol). The solution was warmed to ambient temperature. After 15 minutes, the solution was quenched with water, extracted with EtOAc, dried, and concentrated. HPLC purification gave the title compound (0.0066 g, 6%) as a white solid. $^1$H NMR (400 MHz, CDCl$_3$) δ 1.69-1.76 (m, 1H), 1.81-1.88 (m, 1H), 1.86-2.12 (m, 2H), 2.04 (s, 3H), 2.26 (s, 6H) 2.60 (t, 2H), 2.78-2.85 (m, 1H), 2.95-3.04 (m, 1H), 3.13-3.21 (m, 1H), 3.54-3.60 (m, 2H), 3.78-3.84 (m, 1H), 4.41-4.46 (m, 1H), 6.15 (s, 1H), 7.40 (s, 1H), 7.53 (d, 1H), 7.59-7.64 (m, 3H), 8.49 (s, 1H).

Example 14

1-(4-(2-(4-(2-Methylpyridin-3-yloxy)-5-(thieno[3,2-b]pyridin-7-ylthio)pyridin-2-ylamino)thiazol-4-yl)piperidin-1-yl)ethanone

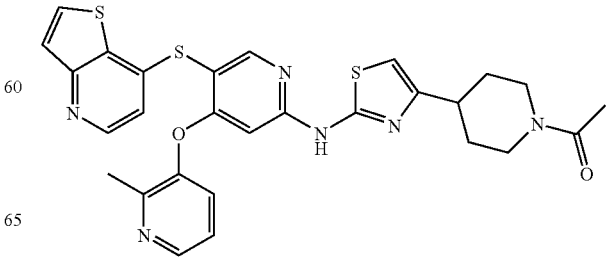

Step A: Preparation of 3-(2-chloropyridin-4-yloxy)-2-methylpyridine: Sodium hydride (1.07 g, 42.3 mmol) was added to DMF (25 mL). 3-Hydroxy-2-methylpyridine (4.40 g, 40.3 mmol) was slowly added to the mixture and the reaction was stirred for 1 hour. 2-Chloro-4-nitropyridine (6.71 g, 42.3 mmol) was added and the reaction was stirred overnight at ambient temperature. Water was added and the reaction mixture was extracted with ethyl acetate. The organic layer was washed with water, dried and concentrated to give the title compound (8.0 g, 90% yield) as a yellow oil, which solidified upon standing at ambient temperature.

Step B: Preparation of tert-butyl 4-(2-methylpyridin-3-yloxy)pyridin-2-ylcarbamate: 3-(2-Chloropyridin-4-yloxy)-2-methylpyridine (4.8 g, 21.8 mmol), tert-butyl carbamate (6.37 g, 54.4 mmol), and potassium phosphate (5.08 g, 23.9 mmol) were added to degassed toluene (100 mL). 9,9-Dimethyl-4,5-bis(diphenylphosphino)xanthene (0.944 g, 1.63 mmol), tris(dibenzylideneacetone)-dipalladium (0.996 g, 1.09 mmol) and degassed water (25 mL) were added, and the reaction was stirred at 90° C. for 3 days. The reaction mixture was diluted with water and extracted with ethyl acetate. The organic layer was dried, concentrated, and flash chromatographed (10-50% ethyl acetate/hexanes) to give the title compound (5.5 g, 59% yield) as a light yellow solid.

Step C: Preparation of 4-(2-methylpyridin-3-yloxy)pyridin-2-amine: tert-Butyl 4-(2-methylpyridin-3-yloxy)pyridin-2-ylcarbamate (5.5 g, 18.3 mmol) was diluted in dichloromethane (20 mL). Trifluoroacetic acid (20 mL) was added and the reaction was stirred for 3 hours at ambient temperature. The reaction was concentrated, and saturated sodium bicarbonate solution was added to the residue. The aqueous layer was extracted with ethyl acetate and organic layer was dried and concentrated to give the title compound (3.67 g, 99% yield) as light yellow oil.

Step D: Preparation of 5-bromo-4-(2-methylpyridin-3-yloxy)pyridin-2-amine: To 4-(2-methylpyridin-3-yloxy)pyridin-2-amine (3.67 g, 18.2 mmol) in acetic acid (50 mL) was added bromine (0.94 ml, 18.2 mmol). The reaction was stirred at ambient temperature for 5 minutes. Ammonium acetate (1.41 g, 18.2 mmol) was added. After 5 minutes, the solution was concentrated and saturated sodium bicarbonate solution was added. The reaction was extracted with ethyl acetate, dried and concentrated to give the title compound (5.0 g, 98% yield) as light yellow solid.

Step E: Preparation of 1-Benzoyl-3-(5-bromo-4-(2-methylpyridin-3-yloxy)pyridin-2-yl)thiourea: 5-Bromo-4-(2-methylpyridin-3-yloxy)pyridin-2-amine (2.0 g, 7.14 mmol) and benzoyl isothiocyanate (1.0 ml, 7.5 mmol) were diluted in tetrahydrofuran (100 mL) and stirred at ambient temperature overnight. The solution was concentrated and charged with a mixture of ethyl acetate (10 mL) and hexanes (200 mL). The mixture was stirred for 10 minutes and filtered to give the title compound (2.8 g, 89% yield) as yellow solid.

Step F: Preparation of 1-(5-Bromo-4-(2-methylpyridin-3-yloxy)pyridin-2-yl)thiourea: 1-Benzoyl-3-(5-bromo-4-(2-methylpyridin-3-yloxy)pyridin-2-yl)thiourea (2.8 g, 6.3 mmol) and potassium carbonate (0.57 mL, 9.5 mmol) were diluted in ethanol (50 mL). The reaction was stirred at 40° C. for 5 hours, then concentrated and purified using silica gel column chromatography (eluting with ethyl acetate) to give the title compound (1.58 g, 74% yield) as light yellow solid.

Step G: Preparation of tert-butyl 4-(2-(5-bromo-4-(2-methylpyridin-3-yloxy)pyridin-2-ylamino)thiazol-4-yl)piperidine-1-carboxylate: 1-(5-Bromo-4-(2-methylpyridin-3-yloxy)pyridin-2-yl)thiourea (1.48 g, 4.4 mmol), tert-butyl 4-(2-bromoacetyl)piperidine-1-carboxylate (1.41 g, 4.60 mmol, prepared from 1-(tert-butoxycarbonyl)piperidine-4-carboxylic acid utilizing the procedure from Example 1, steps A-C), and triethylamine (0.93 mL, 6.56 mmol) were diluted in ethanol (130 mL). The reaction was stirred at 70° C. overnight and then concentrated. Water was added and the solution was extracted with ethyl acetate, dried and concentrated to give the title compound (2.37 g, 94% yield) as light yellow solid.

Step H: Preparation of 7-chlorothieno[3,2-b]pyridine: A mixture of thieno[3,2-b]pyridin-7-ol (2.50 g, 16.5 mmol) and $POCl_3$ (3.1 mL, 33 mmol) in dichloroethane (10 mL) was stirred for 2 hours at reflux. The mixture was concentrated and the dark residue was resuspended in dichloromethane (50 mL). The solution was carefully neutralized with saturated $NaHCO_3$ solution. The mixture was extracted with dichloromethane, dried over $MgSO_4$, and concentrated to give the title compound (2.09 g, 74%) as a brown solid.

Step I: Preparation of thieno[3,2-b]pyridine-7-thiol: 7-chlorothieno[3,2-b]pyridine (1.0 g, 5.9 mmol) in EtOH (15 mL) was treated with sodium hydrogen sulfide dihydrate (3.26 g, 35.4 mmol). The solution was heated at 90° C. overnight. An additional amount of sodium hydrogen sulfide dihydrate (3.26 g, 35.4 mmol) was added and the reaction stirred an additional 20 hours at reflux. The solution was cooled to ambient temperature and diluted with water (100 mL) to dissolve the solids. The solution was cooled to 0° C. and concentrated hydrochloric acid solution was added slowly to adjust the pH to 1. The solution was then filtered and the solid was dried under high vacuum to provide thieno[3,2-b]pyridine-7-thiol (0.73 g, 74% yield) as a yellow solid.

Step J: Preparation of 7-(2-(thieno[3,2-b]pyridin-7-yl)disulfanyl)thieno[3,2-b]pyridine: Thieno[3,2-b]pyridine-7-thiol (1.00 g, 5.9 mmol) was dissolved in dichloromethane (40 mL). The solution was cooled to 0° C. and sulfuryl chloride (1M in dichloromethane, 2.9 mL, 2.9 mmol) was added dropwise and the reaction stirred while warming to ambient temperature. The solution stirred for 5 hours at ambient temperature and then concentrated to dryness. The residue was left standing under open air for two days. The residue was then diluted in dichloromethane and was neutralized with saturation $NaHCO_3$ solution. The organic layer was separated, dried, and concentrated. The residue was triturated with ether and the solid was filtered and dried to provide the title compound (0.37 g, 46% yield) as a tan solid.

Step K: Preparation of tert-Butyl 4-(2-(4-(2-methylpyridin-3-yloxy)-5-(thieno[3,2-b]pyridin-7-ylthio)pyridin-2-ylamino)thiazol-4-yl)piperidine-1-carboxylate: tert-Butyl 4-(2-(5-bromo-4-(2-methylpyridin-3-yloxy)pyridin-2-ylamino)thiazol-4-yl)piperidine-1-carboxylate (0.045 g, 0.082 mmol) was dissolved in tetrahydrofuran (5 mL). The solution was cooled to −78° C. and methyllithium (1.6M in ether, 0.064 mL, 0.10 mmol) was added. The reaction was stirred for 5 minutes and then butyllithium (2.5 M in hexanes, 0.041 ml, 0.10 mmol) was added. After 5 minutes, 7-(2-(thieno[3,2-b]pyridin-7-yl)disulfanyl)thieno[3,2-b]pyridine (0.033 g, 0.099 mmol) was added. After stirring for an additional 5 minutes, water added and the solution was allowed to warm to ambient temperature. The reaction mixture was extracted with ethyl acetate, dried and concentrated. The residue was purified by reverse phase HPLC purification to provide the title compound (0.013 g, 25% yield) as an off white solid.

Step L: Preparation of 4-(2-methylpyridin-3-yloxy)-N-(4-(piperidin-4-yl)thiazol-2-yl)-5-(thieno[3,2-b]pyridin-7-ylthio)pyridin-2-amine dihydrochloride: tert-Butyl 4-(2-(4-(2-methylpyridin-3-yloxy)-5-(thieno[3,2-b]pyridin-7-ylthio)pyridin-2-ylamino)thiazol-4-yl)piperidine-1-carboxylate (0.14 g, 0.22 mmol was dissolved in dichloromethane (2 mL) and charged with HCl (2N in diethyl ether, 3 mL). After stirring at ambient temperature for 2 hours, the solution was concentrated and dried under high vacuum to give the title compound (0.10 g, 75% yield) as a white solid.

Step M: Preparation of 1-(4-(2-(4-(2-methylpyridin-3-yloxy)-5-(thieno[3,2-b]pyridin-7-ylthio)pyridin-2-ylamino)thiazol-4-yl)piperidin-1-yl)ethanone: 4-(2-Methylpyridin-3-yloxy)-N-(4-(piperidin-4-yl)thiazol-2-yl)-5-(thieno[3,2-b]pyridin-7-ylthio)pyridin-2-amine dihydrochloride (0.051 g, 0.08 mmol) was dissolved in dichloromethane (2 mL). Triethylamine (0.10 mL, 0.74 mmol) and acetic anhydride (0.017 mL, 0.19 mmol) were added and the reaction was stirred at ambient temperature overnight. Saturated sodium bicarbonate solution was added, and the reaction was extracted with ethyl acetate. The organic layer was dried and concentrated to give the title compound (0.051 g, 70% yield) as yellow solid. $^1$H NMR (400 MHz, CDCl$_3$) δ 8.57 (s, 1H), 8.50 (d, 1H), 8.41 (dd, 1H), 7.73 (d, 1H), 7.56 (d, 1H), 7.19 (m, 1H), 7.17 (m, 1H), 6.92 (d, 1H), 6.40 (d, 1H), 6.36 (s, 1H), 4.67 (m, 1H), 3.86 (m, 1H), 3.13 (m, 1H), 2.69 (m, 2H), 2.16 (s, 3H), 1.94 (m, 2H), 1.60 (m, 2H).

Example 15

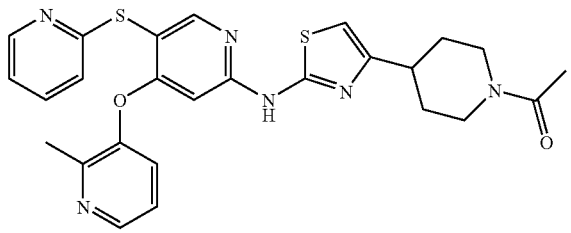 [SMILES: CC(=O)N1CCC(c2csc(Nc3cc(Oc4cccnc4C)c(Sc4ccccn4)cn3)n2)CC1]

1-(4-(2-(4-(2-Methylpyridin-3-yloxy)-5-(pyridin-2-ylthio)pyridin-2-ylamino)thiazol-4-yl)piperidin-1-yl)ethanone Step A: Preparation of tert-butyl 4-(2-(4-(2-methylpyridin-3-yloxy)-5-(pyridin-2-ylthio)pyridin-2-ylamino)thiazol-4-yl)piperidine-1-carboxylate: Prepared from tert-butyl 4-(2-(5-bromo-4-(2-methylpyridin-3-yloxy)pyridin-2-ylamino)thiazol-4-yl)piperidine-1-carboxylate using the method of Example 16, Step B.

Step B: Preparation of 1-(4-(2-(4-(2-methylpyridin-3-yloxy)-5-(pyridin-2-ylthio)pyridin-2-ylamino)thiazol-4-yl)piperidin-1-yl)ethanone: Prepared from tert-butyl 4-(2-(4-(2-methylpyridin-3-yloxy)-5-(pyridin-2-ylthio)pyridin-2-ylamino)thiazol-4-yl)piperidine-1-carboxylate according to the method of Example 14, Steps L and M. $^1$H NMR (400 MHz, CDCl$_3$) δ 8.50 (s, 1H), 8.39 (m, 1H), 8.38 (m, 1H), 7.51 (dt, 1H), 7.29 (dd, 1H), 7.17 (dd, 1H), 7.10 (m, 1H), 7.02 (m, 1H), 6.39 (s, 1H), 6.36 (d, 1H), 4.65 (d, 1H), 3.85 (d, 1H), 3.12 (m, 1H), 2.67 (m, 2H), 2.27 (s, 3H), 2.10 (s, 3H), 1.94 (t, 2H), 1.50 (m, 2H).

Example 16

1-(4-(5-(4-(2,6-dichlorophenoxy)-5-(pyridin-2-ylthio)pyridin-2-ylamino)-1,2,4-thiadiazol-3-yl)piperidin-1-yl)ethanone

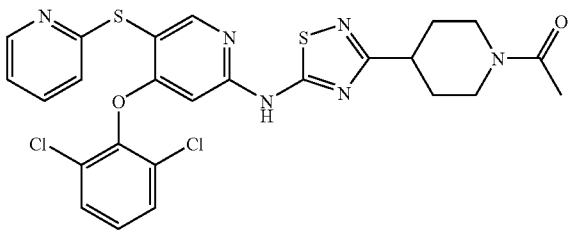 [SMILES: CC(=O)N1CCC(c2nsc(Nc3cc(Oc4c(Cl)cccc4Cl)c(Sc4ccccn4)cn3)n2)CC1]

Step A: Preparation of tert-Butyl 4-(5-(5-bromo-4-(2,6-dichlorophenoxy)pyridin-2-ylamino)-1,2,4-thiadiazol-3-yl)piperidine-1-carboxylate: tert-Butyl 4-(Chloro(methylsulfonyloxyimino)methyl)piperidine-1-carboxylate (1.16 g, 3.4 mmol), pyridine (0.96 mL, 11.8 mmol), NaSCN (0.28 g, 3.4 mmol), and 5-bromo-4-(2,6-dichlorophenoxy)pyridin-2-amine (0.88 g, 2.6 mmol, prepared from 2,6-dichlorophenol according to the procedure of Example 14, steps A-D) were reacted in acetonitrile (20 mL) according to the conditions described in Example 7, step I, to provide the title compound.

Step B: Preparation of tert-Butyl 4-(5-(4-(2,6-dichlorophenoxy)-5-(pyridin-2-ylthio)pyridin-2-ylamino)-1,2,4-thiadiazol-3-yl)piperidine-1-carboxylate: tert-Butyl 4-(5-(5-bromo-4-(2,6-dichlorophenoxy)pyridin-2-ylamino)-1,2,4-thiadiazol-3-yl)piperidine-1-carboxylate (0.080 g, 0.13 mmol), methyllithium (0.092 ml, 0.15 mmol), butyllithium (0.056 mL, 0.15 mmol) and 2-(2-(pyridin-2-yl)disulfanyl)pyridine (0.038 g, 0.17 mmol) were reacted according to the procedure in Example 14, Step K, to give the title compound (0.015 g, 18% yield) as a white solid.

Step C: Preparation of 4-(2,6-dichlorophenoxy)-N-(3-(piperidin-4-yl)-1,2,4-thiadiazol-5-yl)-5-(pyridin-2-ylthio)pyridin-2-amine dihydrochloride: Prepared from tert-Butyl 4-(5-(4-(2,6-dichlorophenoxy)-5-(pyridin-2-ylthio)pyridin-2-ylamino)-1,2,4-thiadiazol-3-yl)piperidine-1-carboxylate according to the method of Example 10.

Step D: Preparation of 1-(4-(5-(4-(2,6-dichlorophenoxy)-5-(pyridin-2-ylthio)pyridin-2-ylamino)-1,2,4-thiadiazol-3-yl)piperidin-1-yl)ethanone: Prepared from 4-(2,6-dichlorophenoxy)-N-(3-(piperidin-4-yl)-1,2,4-thiadiazol-5-yl)-5-(pyridin-2-ylthio)pyridin-2-amine dihydrochloride according to the method of Example 13. $^1$H NMR (400 MHz, CDCl$_3$) δ 1.72-1.88 (m, 4H), 1.99 (s, 3H), 2.84-3.02 (m, 2H), 3.17 (t, 1H), 3.79 (d, 1H), 4.41 (d, 1H), 6.04 (s, 1H), 6.97-7.00 (m, 1H), 7.06 (d, 1H), 7.18 (t, 1H), 7.35 (d, 2H), 7.46 (t, 1H), 8.38 (d, 1H), 8.61 (s, 1H), 9.36 (bs, 1H).

Example 17

1-(4-(2-(5-(3-Methoxyphenylthio)-4-(2-methylpyridin-3-yloxy)pyridin-2-ylamino)thiazol-4-yl)piperidin-1-yl)ethanone

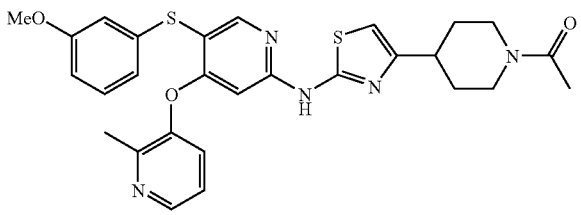 [SMILES: COc1cccc(Sc2cnc(Nc3nc(C4CCN(C(C)=O)CC4)cs3)cc2Oc2cccnc2C)c1]

Step A: Preparation of tert-butyl 4-(2-(5-(3-methoxyphenylthio)-4-(2-methylpyridin-3-yloxy)pyridin-2-ylamino)thiazol-4-yl)piperidine-1-carboxylate: tert-Butyl 4-(2-(5-bromo-4-(2-methylpyridin-3-yloxy)pyridin-2-ylamino)thiazol-4-yl)piperidine-1-carboxylate (0.15 g, 0.27 mmol), Pd$_2$dba$_3$ (0.25 g, 0.27 mmol), Xantphos (0.20 g, 0.34 mmol), and K$_3$PO$_4$ (0.175 g, 0.823 mmol) were suspended in degassed toluene (2 mL). 3-Methoxybenzenethiol (0.068 mL, 0.55 mmol) was added. The mixture was stirred at 130° C. for 3 hours in a sealed tube. The solution was cooled and flash chromatographed (40-50% EtOAc/hexanes) to afford the title compound (0.084 g, 51% yield) as an off-white solid.

Step B: 5-(3 Methoxyphenylthio)-4-(2-methylpyridin-3-yloxy)-N-(4-(piperidin-4-yl)thiazol-2-yl)pyridin-2-amine dihydrochloride: Prepared from tert-butyl 4-(2-(5-(3-methoxyphenylthio)-4-(2-methylpyridin-3-yloxy)pyridin-2-ylamino)thiazol-4-yl)piperidine-1-carboxylate according to the method of Example 10.

Step C: 1-(4-(2-(5-(3-Methoxyphenylthio)-4-(2-methylpyridin-3-yloxy)pyridin-2-ylamino)thiazol-4-yl)piperidin-1-yl)ethanone: Prepared from 5-(3Methoxyphenylthio)-4-(2-methylpyridin-3-yloxy)-N-(4-(piperidin-4-yl)thiazol-2-yl)pyridin-2-amine dihydrochloride according to the method of Example 13. $^1$H NMR (400 MHz, CDCl$_3$) δ 1.43-1.58 (m, 2H), 1.96 (t, 2H), 2.09 (s, 3H), 2.22 (s, 3H), 2.61-2.71 (m, 2H), 3.12 (t, 1H), 3.75 (s, 3H), 3.85 (d, 1H), 4.64 (d, 1H), 6.35 (d, 2H), 6.71-6.74 (m, 1H), 6.82-6.85 (m, 2H), 7.16-7.20 (m, 2H), 7.23 (s, 1H), 8.39-8.41 (m, 1H), 9.04 (s, 1H).

Example 18

1-(4-(5-(4-(2-Methylpyridin-3-yloxy)-5-(pyridin-2-ylthio)pyridin-2-ylamino)-1,2,4-thiadiazol-3-yl)piperidin-1-yl)ethanone

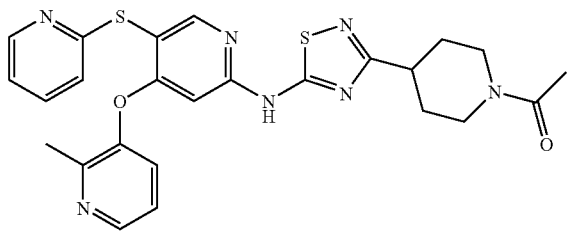

Step A: Preparation of tert-butyl 4-(5-(5-bromo-4-(2-methylpyridin-3-yloxy)pyridin-2-ylamino)-1,2,4-thiadiazol-3-yl)piperidine-1-carboxylate: Prepared from 5-bromo-4-(2-methylpyridin-3-yloxy)pyridin-2-amine according to the method of Example 7, Step I.

Step B: tert-Butyl 4-(5-(4-(2-methylpyridin-3-yloxy)-5-(pyridin-2-ylthio)pyridin-2-ylamino)-1,2,4-thiadiazol-3-yl)piperidine-1-carboxylate: Prepared from tert-butyl 4-(5-(5-bromo-4-(2-methylpyridin-3-yloxy)pyridin-2-ylamino)-1,2,4-thiadiazol-3-yl)piperidine-1-carboxylate according to the method of Example 16, Step B.

Step C: N-(4-(2-Methylpyridin-3-yloxy)-5-(pyridin-2-ylthio)pyridin-2-yl)-3-(piperidin-4-yl)-1,2,4-thiadiazol-5-amine dihydrochloride: Prepared from tert-Butyl 4-(5-(4-(2-methylpyridin-3-yloxy)-5-(pyridin-2-ylthio)pyridin-2-ylamino)-1,2,4-thiadiazol-3-yl)piperidine-1-carboxylate according to the method of Example 10.

Step D: 1-(4-(5-(4-(2-Methylpyridin-3-yloxy)-5-(pyridin-2-ylthio)pyridin-2-ylamino)-1,2,4-thiadiazol-3-yl)piperidin-1-yl)ethanone. Prepared from N-(4-(2-Methylpyridin-3-yloxy)-5-(pyridin-2-ylthio)pyridin-2-yl)-3-(piperidin-4-yl)-1,2,4-thiadiazol-5-amine dihydrochloride according to the method of Example 13. $^1$H NMR (400 MHz, CDCl$_3$) δ 10.63 (s, 1H), 8.59 (s, 1H), 8.37 (m, 2H), 7.52 (dt, 1H), 7.31 (dd, 1H), 7.18 (dd, 1H), 7.13 (m, 1H), 7.02 (m, 1H), 6.26 (s, 1H), 4.40 (m, 1H), 3.80 (m, 1H), 3.21 (m, 1H), 2.98 (m, 2H), 2.26 (s, 3H), 2.09 (m, 2H), 1.95 (s, 3H), 1.84 (m, 2H).

Example 19

1-(4-(5-(5-Bromo-4-(2-methylpyridin-3-yloxy)pyridin-2-ylamino)-1,2,4-thiadiazol-3-yl)piperidin-1-yl)ethanone

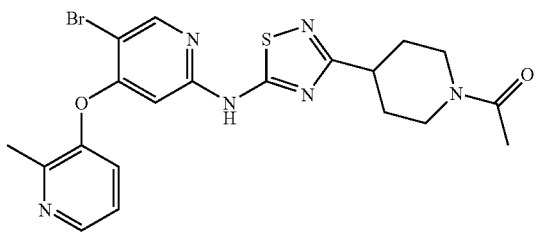 [SMILES: CC(=O)N1CCC(c2nsc(Nc3cc(Oc4cccnc4C)c(Br)cn3)n2)CC1]

Step A: N-(5-Bromo-4-(2-methylpyridin-3-yloxy)pyridin-2-yl)-3-(piperidin-4-yl)-1,2,4-thiadiazol-5-amine dihydrochloride: Prepared from tert-butyl 4-(5-(5-bromo-4-(2-methylpyridin-3-yloxy)pyridin-2-ylamino)-1,2,4-thiadiazol-3-yl)piperidine-1-carboxylate according to the method of Example 10.

Step B: 1-(4-(5-(5-Bromo-4-(2-methylpyridin-3-yloxy)pyridin-2-ylamino)-1,2,4-thiadiazol-3-yl)piperidin-1-yl)ethanone: Prepared from N-(5-Bromo-4-(2-methylpyridin-3-yloxy)pyridin-2-yl)-3-(piperidin-4-yl)-1,2,4-thiadiazol-5-amine dihydrochloride according to the method of Example 13. $^1$H NMR (400 MHz, CDCl$_3$) δ 10.12 (s, 1H), 8.50 (d, 1H), 8.46 (m, 1H), 7.41 (m, 1H), 7.25 (m, 1H), 6.23 (s, 1H), 4.41 (m, 1H), 3.80 (m, 1H), 3.21 (m, 1H), 2.97 (m, 2H), 2.44 (s, 3H), 2.09 (m, 2H), 1.96 (s, 3H), 1.85 (m, 2H)

Example A

In Vitro Glucokinase Assays

The in vitro efficacy of glucokinase activators of the present invention was assessed in two separate assays: an EC$_{50}$ assay to evaluate the potency of each compound at a fixed, physiologically relevant concentration of glucose, and a glucose S$_{0.5}$ assay at a fixed, near saturating (if possible) concentration of compound to evaluate its effect on the V$_m$ and S$_{0.5}$ for glucose. For each of these assays, glucokinase activity was estimated by monitoring the increase in absorbance at 340 nm in a coupled assay system containing NAD$^+$ and glucose 6-phosphate dehydrogenase. Assays were conducted at 30° C. using a thermostatically controlled absorbance plate reader (Spectramax 340PC, Molecular Devices Corp.) and clear, 96-well, flat bottom, polystyrene plates (Costar 3695, Corning). Each 50-μL assay mixture contained 10 mM K$^-$MOPS, pH 7.2, 2 mM MgCl$_2$, 50 mM KCl, 0.01% Triton X-100, 2% DMSO, 1 mM DTT, 1 mM ATP, 1 mM NAD$^+$, 5 U/mL glucose 6-phosphate dehydrogenase, approximately 5 nM human glucokinase and (depending on the assay) varying concentrations of glucose and test compound. The absorbance at 340 nm was monitored kinetically over a period of 5 minutes (10 s/cycle), and rates were estimated from the slopes of linear fits to the raw data.

Glucokinase EC$_{50}$ Assay:

For this assay, the glucose concentration was fixed at 5 mM, while the control or test compound was varied over a 10-point, 3-fold dilution series and typically ranged from a high dose of 50 μM to a low dose of approximately 2.5 nM. A standard, four-parameter logistic model (Equation 1) was fit to the raw data (rate versus concentration of compound):

$$y = A + \frac{B - A}{1 + \left[\frac{C}{x}\right]^D} \quad (1)$$

where x is the concentration of compound, y is the estimated rate, A and B are the lower and upper asymptotes, respectively, C is the $EC_{50}$ and D is the Hill slope. The $EC_{50}$ is defined as the midpoint or inflection point between the upper and lower asymptotes. A compound was identified as a glucokinase activator if it stimulated the activity of glucokinase 25 percent or more above that observed in the absence of the compound.

Certain compounds exemplified herein have been found to have an $EC_{50}$ in the range of 2 and 5000 nM.

Glucose $S_{0.5}$ Assay:

For this assay, the concentration of control or test compound was fixed at or near a saturating concentration, if possible, typically 50 μM, while the glucose concentration was varied over a 10-point, 2-fold dilution series ranging from 80 to approximately 0.16 mM. The same four-parameter logistic model used for the $EC_{50}$ assay (Equation 1) was employed to estimate the relevant kinetic parameters. In this assay, the definitions for the variables and parameters are similar except that x represents the concentration of glucose, B is the rate at saturating glucose ($V_m$), C is the $S_{0.5}$ for glucose (the concentration of glucose at $V_m/2$) and D is the Hill Coefficient. The $S_{0.5}$ for compounds of the Examples (with the exception of the "representative compounds") is in the range of 1.5 and 7.5 mM.

For certain compounds of the invention, the $S_{0.5}$ is in the range of 1.5 and 4.0 mM. Particular compounds exemplified herein have been found to have an $S_{0.5}$ of between 0.3 and 5 mM in the above described assay.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound selected from
    1-(4-(2-(4-(2-Methylpyridin-3-yloxy)-5-(thieno[3,2-b]pyridin-7-ylthio)pyridin-2-ylamino)thiazol-4-yl)piperidin-1-yl)ethanone;
    1-(4-(2-(4-(2-Methylpyridin-3-yloxy)-5-(pyridin-2-ylthio)pyridin-2-ylamino)thiazol-4-yl)piperidin-1-yl)ethanone;
    1-(4-(2-(5-(3-Methoxyphenylthio)-4-(2-methylpyridin-3-yloxy)pyridin-2-ylamino)thiazol-4-yl)piperidin-1-yl)ethanone;
    1-(4-(5-(4-(2-Methylpyridin-3-yloxy)-5-(pyridin-2-ylthio)pyridin-2-ylamino)-1,2,4-thiadiazol-3-yl)piperidin-1-yl)ethanone;
    1-(4-(5-(5-Bromo-4-(2-methylpyridin-3-yloxy)pyridin-2-ylamino)-1,2,4-thiadiazol-3-yl)piperidin-1-yl)ethanone
    and pharmaceutically acceptable salts thereof.

2. A pharmaceutical composition comprising a compound of claim 1, or a pharmaceutically acceptable salt thereof and a pharmaceutically acceptable diluent or carrier.

* * * * *